United States Patent
Ford et al.

(10) Patent No.: US 10,087,180 B2
(45) Date of Patent: Oct. 2, 2018

(54) PYRAZOLO-PYRIDINE DERIVATIVES AS KINASE INHIBITORS

(71) Applicants: UCB Biopharma SPRL, Brussels (BE); Katholieke Universiteit Leuven, K.U.Leuven R&D, Leuven (BE)

(72) Inventors: Daniel James Ford, Slough (GB); James Thomas Reuberson, Slough (GB)

(73) Assignee: UCB BIOPHARMA SPRL, Brussels (BE)

( * ) Notice: Subject to any disclaimer, the term of this patent is extended or adjusted under 35 U.S.C. 154(b) by 0 days.

(21) Appl. No.: 15/318,473

(22) PCT Filed: Jun. 11, 2015

(86) PCT No.: PCT/EP2015/063048
§ 371 (c)(1),
(2) Date: Dec. 13, 2016

(87) PCT Pub. No.: WO2015/193167
PCT Pub. Date: Dec. 23, 2015

(65) Prior Publication Data
US 2017/0121324 A1    May 4, 2017

(30) Foreign Application Priority Data
Jun. 17, 2014 (GB) .................. 1410815.3

(51) Int. Cl.
*C07D 471/04* (2006.01)
*C07D 519/00* (2006.01)
*A61K 31/496* (2006.01)

(52) U.S. Cl.
CPC ......... *C07D 471/04* (2013.01); *C07D 519/00* (2013.01)

(58) Field of Classification Search
None
See application file for complete search history.

(56) References Cited

U.S. PATENT DOCUMENTS

2004/0106635 A1    6/2004    Takamuro et al.
2013/0203768 A1    8/2013    Berger et al.

FOREIGN PATENT DOCUMENTS

| EP | 1 772 454 A1 | 4/2007 |
| WO | 09/089359 A1 | 7/2009 |
| WO | 13/034738 A1 | 3/2013 |
| WO | 14/096423 A1 | 6/2014 |

OTHER PUBLICATIONS

Arita et al. Microbiol Immunol 2015; 59: 338-347.*
Dubuisson et al.Journal of Hepatology 2014 vol. 61 j S3-S13.*
McNamara et al. Nature. Dec. 12, 2013; 504(7479): 248-253.*
Ho et al., "The discovery of potent, selective, and orally active pyrazoloquinolines and PDE10A inhibitors for the treatment of Schizophrenia", Bioorganic and Medicinal Chemistry Letters, 2011, 22(9), 1019-1022.

* cited by examiner

*Primary Examiner* — Emily A Bernhardt
(74) *Attorney, Agent, or Firm* — McDonnell Boehnen Hulbert & Berghoff LLP

(57) ABSTRACT

A series of pyrazolo[3,4-b]pyridine derivatives that are substituted at the 4-position by a diaza monocyclic, bridged bicyclic or spirocyclic moiety, being selective inhibitors of phosphatidylinositol-4-kinase IIIβ (PI4KIIIβ) activity, are beneficial in the treatment and/or prevention of various human ailments, including inflammatory, autoimmune and oncological disorders; viral diseases and malaria; and organ and cell transplant rejection.

12 Claims, No Drawings

PYRAZOLO-PYRIDINE DERIVATIVES AS KINASE INHIBITORS

This application is a US national phase of International Application No. PCT/EP2015/063048, filed Jun. 11, 2015, which claims priority to Great Britain Application No. 1410815.3, filed Jun. 17, 2014.

The present invention relates to a class of fused pyridine derivatives, and to their use in therapy. More particularly, the present invention provides pyrazolo[3,4-b]pyridine derivatives that are substituted at the 4-position by a diaza monocyclic, bridged bicyclic or spirocyclic moiety. These compounds are selective inhibitors of phosphatidylinositol-4-kinase IIIβ (PI4KIIIβ) activity, and are accordingly of benefit as pharmaceutical agents, especially in the treatment of adverse inflammatory, autoimmune and oncological disorders, in the treatment of viral diseases and malaria, and in the management of organ and cell transplant rejection.

In addition, the compounds in accordance with the present invention may be beneficial as pharmacological standards for use in the development of new biological tests and in the search for new pharmacological agents. Thus, the compounds of this invention may be useful as radioligands in assays for detecting pharmacologically active compounds.

WO 2013/034738 discloses that inhibitors of PI4KIIIβ activity are useful as medicaments for the treatment of autoimmune and inflammatory disorders, and organ and cell transplant rejection.

WO 2010/103130 describes a family of oxazolo[5,4-d]pyrimidine, thiazolo[5,4-d]-pyrimidine, thieno[2,3-d]pyrimidine and purine derivatives that are active in a range of assays, including the Mixed Lymphocyte Reaction (MLR) test, and are stated to be effective for the treatment of immune and autoimmune disorders, and organ and cell transplant rejection. WO 2011/147753 discloses the same family of compounds as having significant antiviral activity. Furthermore, WO 2012/035423 discloses the same family of compounds as having significant anticancer activity.

WO 2013/024291, WO 2013/068458, WO 2014/053581, and copending international patent application PCT/EP2013/077846 (published on 26 Jun. 2014 as WO 2014/096423) describe various series of fused pyrimidine derivatives that are stated to be of benefit as pharmaceutical agents, especially in the treatment of adverse inflammatory, autoimmune and oncological disorders, in the treatment of viral diseases, and in the management of organ and cell transplant rejection.

Inhibitors of PI4KIIIβ have been identified as molecules with an ideal activity profile for the prevention, treatment and elimination of malaria (cf. C. W. McNamara et al., *Nature,* 2013, 504, 248-253).

WO 99/51582 describes a class of nitrogen-containing heterocyclic compounds that are stated to have an activity of inhibiting phosphorylation of a platelet-derived growth factor (PDGF) receptor.

None of the prior art available to date, however, discloses or suggests the precise structural class of pyrazolo[3,4-b]pyridine derivatives as provided by the present invention as having activity as PI4KIIIβ inhibitors.

The compounds of the present invention are potent and selective inhibitors of PI4KIIIβ activity, inhibiting the kinase affinity of human PI4KIIIβ ($IC_{50}$) at concentrations of 50 μM or less, generally of 20 μM or less, usually of 5 μM or less, typically of 1 μM or less, suitably of 500 nM or less, ideally of 100 nM or less, and preferably of 20 nM or less (the skilled person will appreciate that a lower $IC_{50}$ figure denotes a more active compound). The compounds of the invention may possess at least a 10-fold selective affinity, typically at least a 20-fold selective affinity, suitably at least a 50-fold selective affinity, and ideally at least a 100-fold selective affinity, for human PI4KIIIβ relative to other human kinases.

Certain compounds in accordance with the present invention are active as inhibitors when subjected to the Mixed Lymphocyte Reaction (MLR) test. The MLR test is predictive of immunosuppression or immunomodulation. Thus, when subjected to the MLR test, certain compounds of the present invention display an $IC_{50}$ value of 10 μM or less, generally of 5 μM or less, usually of 2 μM or less, typically of 1 μM or less, suitably of 500 nM or less, ideally of 100 nM or less, and preferably of 20 nM or less (again, the skilled person will appreciate that a lower $IC_{50}$ figure denotes a more active compound).

The compounds of the invention possess notable advantages in terms of their high potency, demonstrable efficacy at lower doses, and valuable pharmacokinetic and pharmacodynamic properties (including clearance and bioavailability).

The present invention provides a compound of formula (I) or an N-oxide thereof, or a pharmaceutically acceptable salt or solvate thereof:

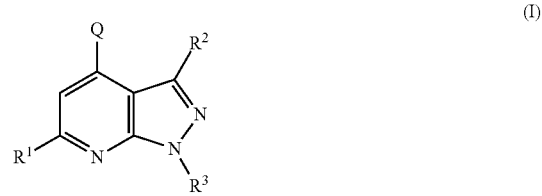

wherein

Q represents a group of formula (Qa), (Qb), (Qc), (Qd) or (Qe):

-continued

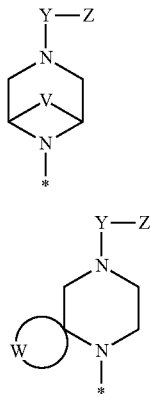
(Qd)

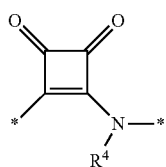
(Qe)

in which the asterisk (*) represents the point of attachment to the remainder of the molecule;

V represents —CH$_2$—, —C(CH$_3$)$_2$—, -CH$_2$CH$_2$— or —CH$_2$CH$_2$CH$_2$—;

W represents the residue of a C$_{3-7}$ cycloalkyl group;

Y represents a covalent bond, or a linker group selected from —C(O)—, —S(O)—, —S(O)$_2$—, —C(O)O—, —C(O)N(R$^4$)—, —C(O)C(O)— and —S(O)$_2$N(R$^4$)—, or a linker group of formula (Ya):

$$\text{(Ya)}$$

in which the asterisk (*) represents the point of attachment to the remainder of the molecule;

Z represents hydrogen; or Z represents C$_{1-6}$ alkyl, C$_{2-6}$ alkenyl, C$_{3-7}$ cycloalkyl, C$_{3-7}$ cycloalkyl(C$_{1-6}$)alkyl, C$_{3-7}$ heterocycloalkyl, C$_{3-7}$ heterocycloalkyl(C$_{1-6}$)alkyl, aryl, aryl(C$_{1-6}$)alkyl, heteroaryl or heteroaryl(C$_{1-6}$)alkyl, any of which groups may be optionally substituted by one or more substituents;

A$^1$ represents hydrogen, cyano or trifluoromethyl; or A$^1$ represents C$_{1-6}$ alkyl, optionally substituted by one or more substituents independently selected from fluoro, —OR$^a$, trifluoromethoxy, —NR$^b$R$^c$, —CO$_2$R$^d$ and —CONR$^b$R$^c$; or A$^1$ represents C$_{3-7}$ cycloalkyl;

A$^2$ represents hydrogen or C$_{1-6}$ alkyl;

R$^1$ and R$^2$ independently represent hydrogen, halogen, cyano, nitro, hydroxy, trifluoromethyl, trifluoromethoxy, —OR$^a$, —SR$^a$, —SOR$^a$, —SO$_2$R$^a$, —NR$^b$R$^c$, —CH$_2$NR$^b$R$^c$, —NR$^c$COR$^d$, —CH$_2$NR$^c$COR$^d$, —NR$^c$CO$_2$R$^d$, —NHCONR$^b$R$^c$, —NR$^c$SO$_2$R$^e$, —N(SO$_2$R$^e$)$_2$, —NHSO$_2$NR$^b$R$^c$, —COR$^d$, —CO$_2$R$^d$, —CONR$^b$R$^c$, —CON(OR$^a$)R$^b$ or —SO$_2$NR$^b$R$^c$; or C$_{1-6}$ alkyl, C$_{3-7}$ cycloalkyl, C$_{3-7}$ cycloalkyl(C$_{1-6}$)alkyl, aryl, aryl (C$_{1-6}$)alkyl, C$_{3-7}$ heterocycloalkyl, C$_{3-7}$ heterocycloalkyl (C$_{1-6}$)alkyl, C$_{3-7}$ heterocycloalkenyl, heteroaryl or heteroaryl(C$_{1-6}$)alkyl, any of which groups may be optionally substituted by one or more substituents;

R$^3$ represents hydrogen; or R$^3$ represents C$_{1-6}$ alkyl, optionally substituted by one or more halogen atoms;

R$^4$ represents hydrogen; or R$^4$ represents C$_{1-6}$ alkyl, optionally substituted by one or more substituents independently selected from —OR$^a$ and —NR$^b$R$^c$;

R$^a$ represents hydrogen; or R$^a$ represents C$_{1-6}$ alkyl, aryl, aryl(C$_{1-6}$)alkyl, heteroaryl or heteroaryl(C$_{1-6}$)alkyl, any of which groups may be optionally substituted by one or more substituents;

R$^b$ and R$^c$ independently represent hydrogen or trifluoromethyl; or C$_{1-6}$ alkyl, C$_{3-7}$ cycloalkyl, C$_{3-7}$ cycloalkyl (C$_{1-6}$)alkyl, aryl, aryl(C$_{1-6}$)alkyl, C$_{3-7}$ heterocycloalkyl, C$_{3-7}$ heterocycloalkyl(C$_{1-6}$)alkyl, heteroaryl or heteroaryl(C$_{1-6}$) alkyl, any of which groups may be optionally substituted by one or more substituents; or R$^b$ and R$^c$, when taken together with the nitrogen atom to which they are both attached, represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents;

R$^d$ represents hydrogen; or C$_{1-6}$ alkyl, C$_{3-7}$ cycloalkyl, aryl, C$_{3-7}$ heterocycloalkyl or heteroaryl, any of which groups may be optionally substituted by one or more substituents; and R$^e$ represents C$_{1-6}$ alkyl, aryl or heteroaryl, any of which groups may be optionally substituted by one or more substituents.

Where any of the groups in the compounds of formula (I) above is stated to be optionally substituted, this group may be unsubstituted, or substituted by one or more substituents. Typically, such groups will be unsubstituted, or substituted by one or two substituents.

For use in medicine, the salts of the compounds of formula (I) will be pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example, be formed by mixing a solution of the compound of the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

Suitable alkyl groups which may be present on the compounds of the invention include straight-chained and branched C$_{1-6}$ alkyl groups, for example C$_{1-4}$ alkyl groups. Typical examples include methyl and ethyl groups, and straight-chained or branched propyl, butyl, pentyl and hexyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

Suitable $C_{2-6}$ alkenyl groups include vinyl, allyl and prop-1-en-2-yl.

Suitable $C_{3-7}$ cycloalkyl groups, which may comprise benzo-fused analogues thereof, include cyclopropyl, cyclobutyl, cyclopentyl, indanyl, cyclohexyl and cycloheptyl.

Suitable aryl groups include phenyl and naphthyl, preferably phenyl.

Suitable aryl($C_{1-6}$)alkyl groups include benzyl, phenylethyl, phenylpropyl and naphthylmethyl.

Suitable heterocycloalkyl groups, which may comprise benzo-fused analogues thereof, include oxetanyl, azetidinyl, tetrahydrofuranyl, dihydrobenzofuranyl, pyrrolidinyl, indolinyl, thiazolidinyl, imidazolidinyl, tetrahydropyranyl, chromanyl, piperidinyl, 1,2,3,4-tetrahydroquinolinyl, 1,2,3,4-tetrahydroisoquinolinyl, piperazinyl, 1,2,3,4-tetrahydroquinoxalinyl, homopiperazinyl, morpholinyl, benzoxazinyl and thiomorpholinyl.

Examples of suitable heterocycloalkenyl groups include oxazolinyl.

Suitable heteroaryl groups include furyl, benzofuryl, dibenzofuryl, thienyl, benzothienyl, dibenzothienyl, pyrrolyl, indolyl, pyrrolo[2,3-b]pyridinyl, pyrrolo[3,2-c]pyridinyl, pyrazolyl, pyrazolo[1,5-a]pyridinyl, pyrazolo[3,4-d]pyrimidinyl, indazolyl, oxazolyl, benzoxazolyl, isoxazolyl, thiazolyl, benzothiazolyl, isothiazolyl, imidazolyl, imidazo[2,1-b]thiazolyl, benzimidazolyl, imidazo[1,2-a]pyridinyl, imidazo[4,5-b]pyridinyl, purinyl, imidazo[1,2-a]pyrimidinyl, imidazo[1,2-a]pyrazinyl, oxadiazolyl, thiadiazolyl, benzothiadiazolyl, triazolyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds of the invention possess two or more asymmetric centres, they may additionally exist as diastereomers. The invention is to be understood to extend to all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C=O$)↔enol ($CH=CHOH$) tautomers or amide ($NHC=O$)↔hydroxyimine ($N=COH$) tautomers. Formula (I) and the formulae depicted hereinafter are intended to represent all individual tautomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^{1}H$, $^{2}H$ (deuterium) or $^{3}H$ (tritium) atom, preferably $^{1}H$. Similarly, by way of example, each individual carbon atom present in formula (I), or in the formulae depicted hereinafter, may be present as a $^{12}C$, $^{13}C$, or $^{14}C$ atom, preferably $^{12}C$.

In a particular embodiment, Q represents a group of formula (Qa) as defined above. In a second embodiment, Q represents a group of formula (Qb) as defined above. In a third embodiment, Q represents a group of formula (Qc) as defined above. In a fourth embodiment, Q represents a group of formula (Qd) as defined above. In a fifth embodiment, Q represents a group of formula (Qe) as defined above.

Where Q represents a group of formula (Qa) as defined above, this may be a group of formula (Qa-1), (Qa-2), (Qa-3), (Qa-4), (Qa-5) or (Qa-6):

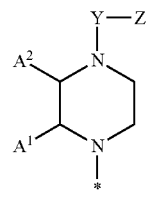
(Qa-1)

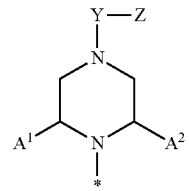
(Qa-2)

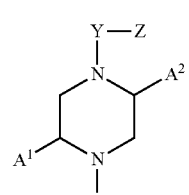
(Qa-3)

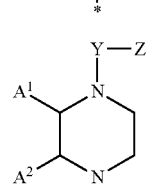
(Qa-4)

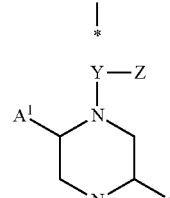
(Qa-5)

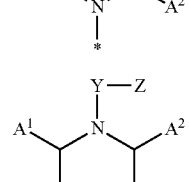
(Qa-6)

in which the asterisk (*) represents the point of attachment to the remainder of the molecule; and Y, Z, $A^1$ and $A^2$ are as defined above.

In a first embodiment, Q represents a group of formula (Qa-1) as defined above.

In a second embodiment, Q represents a group of formula (Qa-2) as defined above.

In a third embodiment, Q represents a group of formula (Qa-3) as defined above.

In a fourth embodiment, Q represents a group of formula (Qa-4) as defined above.

In a fifth embodiment, Q represents a group of formula (Qa-5) as defined above.

In a sixth embodiment, Q represents a group of formula (Qa-6) as defined above.

In one embodiment, V represents —$CH_2$— or —$C(CH_3)_2$—. In a first aspect of that embodiment, V represents —$CH_2$—. In a second aspect of that embodiment, V represents —$C(CH_3)_2$—. Where Q represents a group of formula (Qb) and V represents —$CH_2$— or —$C(CH_3)_2$—, the bicyclic moiety containing the integer V is a 2,5-diazabicyclo[2.2.1]-heptane ring system. Where Q represents a group of formula (Qc) or (Qd) and V represents —$CH_2$— or —$C(CH_3)_2$—, the bicyclic moiety containing the integer V is a 3,6-diazabicyclo[3.1.1]heptane ring system.

In another embodiment, V represents —$CH_2CH_2$—. Where Q represents a group of formula (Qb) and V represents —$CH_2CH_2$—, the bicyclic moiety containing the integer V is a 2,5-diazabicyclo[2.2.2]octane ring system. Where Q represents a group of formula (Qc) or (Qd) and V represents —$CH_2CH_2$—, the bicyclic moiety containing the integer V is a 3,8-diazabicyclo[3.2.1]octane ring system.

In a further embodiment, V represents —$CH_2CH_2CH_2$—. Where Q represents a group of formula (Qb) and V represents —$CH_2CH_2CH_2$—, the bicyclic moiety containing the integer V is a 6,8-diazabicyclo[3.2.2]nonane ring system. Where Q represents a group of formula (Qc) or (Qd) and V represents —$CH_2CH_2CH_2$—, the bicyclic moiety containing the integer V is a 7,9-diazabicyclo[3.3.1]nonane ring system.

Where Q represents a group of formula (Qe), the $C_{3-7}$ cycloalkyl group of which W is the residue is spiro-fused to the adjacent six-membered ring containing two nitrogen atoms. The cyclic group of which W is the residue is selected from cyclopropyl, cyclobutyl, cyclopentyl, cyclohexyl and cycloheptyl. Suitably, the cyclic group of which W is the residue is a $C_{4-6}$ cycloalkyl group. In a particular embodiment, the cyclic group of which W is the residue is cyclobutyl.

Generally, Y represents a covalent bond, or a linker group selected from —C(O)—, —S(O)—, —$S(O)_2$—, —C(O)O—, —C(O)N($R^4$)— and —$S(O)_2$N($R^4$)—, or a linker group of formula (Ya) as defined above.

Typically, Y represents a covalent bond, or a linker group selected from —C(O)—, —C(O)O— and —C(O)N($R^4$)—, or a linker group of formula (Ya) as defined above.

Suitably, Y represents a covalent bond, or a linker group selected from —C(O)— and —C(O)N($R^4$)—.

Appositely, Y represents a covalent bond, or a linker group selected from —C(O)—, —S(O)—, —$S(O)_2$—, —C(O)O—, —C(O)N($R^4$)— and —$S(O)_2$N($R^4$)—.

Suitable values of Y include —C(O)—, —S(O)—, —$S(O)_2$—, —C(O)O—, —C(O)N($R^4$)— and —$S(O)_2$N($R^4$)—.

Typical values of Y include —C(O)—, —C(O)N($R^4$)— and —C(O)C(O)—.

Selected values of Y include —C(O)— and —C(O)N($R^4$)—.

In a first embodiment, Y represents a covalent bond. In a second embodiment, Y represents —C(O)—. In a third embodiment, Y represents —S(O)—. In a fourth embodiment, Y represents —$S(O)_2$—. In a fifth embodiment, Y represents —C(O)O—. In a sixth embodiment, Y represents —C(O)N($R^4$)—. In a seventh embodiment, Y represents —C(O)C(O)—. In an eighth embodiment, Y represents —$S(O)_2$N($R^4$)—. In a ninth embodiment, Y represents a group of formula (Ya) as defined above.

Generally, Z represents hydrogen; or Z represents $C_{1-6}$ alkyl, $C_{3-7}$ cycloalkyl, $C_{3-7}$ cycloalkyl($C_{1-6}$)alkyl, $C_{3-7}$ heterocycloalkyl, $C_{3-7}$ heterocycloalkyl($C_{1-6}$)alkyl, aryl, aryl($C_{1-6}$)alkyl, heteroaryl or heteroaryl($C_{1-6}$)alkyl, any of which groups may be optionally substituted by one or more substituents.

Appositely, Z represents $C_{1-6}$ alkyl, $C_{2-6}$ alkenyl, $C_{3-7}$ cycloalkyl, $C_{3-7}$ cycloalkyl($C_{1-6}$)alkyl, $C_{3-7}$ heterocycloalkyl, $C_{3-7}$ heterocycloalkyl($C_{1-6}$)alkyl, aryl, aryl($C_{1-6}$) alkyl, heteroaryl or heteroaryl($C_{1-6}$)alkyl, any of which groups may be optionally substituted by one or more substituents.

Typically, Z represents $C_{1-6}$ alkyl, $C_{3-7}$ cycloalkyl, $C_{3-7}$ cycloalkyl($C_{1-6}$)alkyl, $C_{3-7}$ heterocycloalkyl, $C_{3-7}$ heterocycloalkyl($C_{1-6}$)alkyl, aryl, aryl($C_{1-6}$)alkyl, heteroaryl or heteroaryl($C_{1-6}$)alkyl, any of which groups may be optionally substituted by one or more substituents.

More typically, Z represents $C_{3-7}$ cycloalkyl, $C_{3-7}$ heterocycloalkyl, aryl or heteroaryl, any of which groups may be optionally substituted by one or more substituents.

Suitably, Z represents aryl or heteroaryl, either of which groups may be optionally substituted by one or more substituents.

In a first embodiment, Z represents hydrogen. In a second embodiment, Z represents optionally substituted $C_{1-6}$ alkyl. In a third embodiment, Z represents optionally substituted $C_{2-6}$ alkenyl. In a fourth embodiment, Z represents optionally substituted $C_{3-7}$ cycloalkyl. In a fifth embodiment, Z represents optionally substituted $C_{3-7}$ cycloalkyl($C_{1-6}$)alkyl. In a sixth embodiment, Z represents optionally substituted $C_{3-7}$ heterocycloalkyl. In a seventh embodiment, Z represents optionally substituted $C_{3-7}$ heterocycloalkyl($C_{1-6}$) alkyl. In an eighth embodiment, Z represents optionally substituted aryl. In a ninth embodiment, Z represents optionally substituted aryl($C_{1-6}$)alkyl. In a tenth embodiment, Z represents optionally substituted heteroaryl. In an eleventh embodiment, Z represents optionally substituted heteroaryl ($C_{1-6}$)alkyl.

In a particular embodiment, Z is other than hydrogen.

Typical values of Z include methyl, ethyl, isopropenyl, cyclopropyl, indanyl, cyclopropylmethyl, cyclopentylethyl, dihydrobenzofuranyl, pyrrolidinyl, indolinyl, dihydrobenzofuranylmethyl, morpholinylmethyl, morpholinylethyl, phenyl, benzyl, phenylethyl, furyl, benzofuryl, thienyl, indolyl, pyrazolyl, indazolyl, isoxazolyl, thiazolyl, benzothiazolyl, imidazolyl, benzimidazolyl, imidazo[1,2-a]pyridinyl, benzothiadiazolyl, pyridinyl, quinolinyl, isoquinolinyl, pyridazinyl, pyrimidinyl, pyrazinyl, quinoxalinyl, indolylmethyl, thiazolylmethyl, imidazo[2,1-b]thiazolylmethyl, pyridinylmethyl, furylethyl, benzimidazolylethyl and pyridinylethyl, any of which groups may be optionally substituted by one or more substituents.

Illustrative values of Z include phenyl, imidazo[1,2-a] pyridinyl, pyridinyl and pyrazinyl, any of which groups may be optionally substituted by one or more substituents.

Suitable values of Z include phenyl, imidazo[1,2-a] pyridinyl and pyridinyl, any of which groups may be optionally substituted by one or more substituents.

In one embodiment, Z is unsubstituted. In another embodiment, Z is substituted by one or more substituents, typically by one, two or three substituents, suitably by one or two substituents. In one aspect of that embodiment, Z is monosubstituted. In another aspect of that embodiment, Z is disubstituted. In a further aspect of that embodiment, Z is trisubstituted.

Typical examples of optional substituents on Z include one or more substituents independently selected from halogen, cyano, nitro, $C_{1-6}$ alkyl, trifluoromethyl, cyano-$(C_{1-6})$alkyl, $(C_{3-7})$heterocycloalkyl, halo$(C_{3-7})$heterocycloalkyl, $(C_{1-6})$alkyl$(C_{3-7})$heterocycloalkyl, $(C_{2-6})$alkoxycarbonyl$(C_{3-7})$heterocycloalkyl, dihalo$(C_{3-7})$heterocycloalkyl, $(C_{3-7})$heterocycloalkyl$(C_{1-6})$alkyl, $(C_{1-6})$alkyl$(C_{3-7})$heterocycloalkyl$(C_{1-6})$alkyl, hetero aryl, hydroxy, oxo, $C_{1-6}$ alkoxy, difluoromethoxy, trifluoromethoxy, trifluoroethoxy $(C_{3-7})$heterocycloalkoxy, $(C_{2-6})$alkoxycarbonyl$(C_{3-7})$heterocycloalkoxy, $(C_{3-7})$heterocycloalkyl$(C_{1-6})$alkoxy, aryloxy, haloaryloxy, $(C_{1-6})$alkoxyaryloxy, $C_{1-3}$ alkylenedioxy, dihalo$(C_{1-3})$alkylenedioxy, arylcarbonyloxy, $C_{1-6}$ alkylthio, $C_{1-6}$ alkylsulfinyl, $C_{1-6}$ alkylsulfonyl, amino, $C_{1-6}$ alkylamino, di$(C_{1-6})$alkylamino, di$(C_{1-6})$-alkylamino$(C_{1-6})$alkyl, arylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, $C_{3-6}$ cycloalkylcarbonyl, $C_{3-6}$ heterocycloalkylcarbonyl, carboxy, $C_{2-6}$ alkoxycarbonyl, aryloxycarbonyl, aminocarbonyl, $C_{1-6}$ alkylaminocarbonyl, di$(C_{1-6})$alkylaminocarbonyl, aminosulfonyl, $C_{1-6}$ alkylaminosulfonyl and di$(C_{1-6})$alkylaminosulfonyl.

Selected examples of optional substituents on Z include one or more substituents independently selected from halogen, cyano, $C_{1-6}$ alkyl, trifluoromethyl, dihalo$(C_{3-7})$-heterocycloalkyl, $C_{1-6}$ alkoxy, difluoromethoxy, trifluoromethoxy and di$(C_{1-6})$alkylamino.

Suitable examples of optional substituents on Z include one or more substituents independently selected from $C_{1-6}$ alkyl, dihalo$(C_{3-7})$heterocycloalkyl, $C_{1-6}$ alkoxy, difluoromethoxy and trifluoromethoxy.

Typical examples of specific substituents on Z include fluoro, chloro, bromo, cyano, nitro, methyl, ethyl, isopropyl, tert-butyl, trifluoromethyl, cyanomethyl, azetidinyl, pyrrolidinyl, piperazinyl, morpholinyl, fluoroazetidinyl, fluoropyrrolidinyl, methylpiperazinyl, tert-butoxycarbonylpiperazinyl, difluoroazetidinyl, difluoropyrrolidinyl, difluoropiperidinyl, pyrrolidinylmethyl, piperidinylmethyl, morpholinylmethyl, methyl-piperazinylmethyl, pyrazolyl, imidazolyl, hydroxy, oxo, methoxy, ethoxy, isopropoxy, difluoromethoxy, trifluoromethoxy, trifluoroethoxy, oxetanyloxy, azetidinyloxy, tetrahydrofuranyloxy, pyrrolidinyloxy, tert-butoxycarbonylazetidinyloxy, tert-butoxycarbonylpyrrolidinyloxy, tetrahydrofuranylmethoxy, morpholinylethoxy, phenoxy, chlorophenoxy, methoxyphenoxy, methylenedioxy, ethylenedioxy, difluoromethylenedioxy, benzoyloxy, methylthio, methylsulfinyl, methylsulfonyl, amino, methylamino, tert-butylamino, dimethylamino, dimethylaminomethyl, phenylamino, acetylamino, methoxycarbonylamino, methylsulfonylamino, formyl, acetyl, cyclopropylcarbonyl, azetidinylcarbonyl, pyrrolidinylcarbonyl, piperidinylcarbonyl, piperazinylcarbonyl, morpholinylcarbonyl, carboxy, methoxycarbonyl, ethoxycarbonyl, tert-butoxycarbonyl, benzyloxycarbonyl aminocarbonyl, methylaminocarbonyl, dimethylaminocarbonyl, aminosulfonyl, methylaminosulfonyl and dimethylaminosulfonyl.

Selected examples of specific substituents on Z include fluoro, chloro, bromo, cyano, methyl, trifluoromethyl, difluoroazetidinyl, methoxy, ethoxy, isopropoxy, difluoromethoxy, trifluoromethoxy and dimethylamino.

Suitable examples of specific substituents on Z include methyl, difluoroazetidinyl, methoxy, ethoxy, isopropoxy, difluoromethoxy and trifluoromethoxy.

Selected values of Z include phenoxymethyl, chlorophenoxymethyl, methoxyphenoxymethyl, tert-butoxycarbonylmethyl, benzyloxycarbonylmethyl, phenoxyethyl, isopropenyl, cyclopropyl, indanyl, cyclopropylmethyl, cyclopentylethyl, (methyl)(oxo)pyrrolidinyl, dihydrobenzofuranyl, methylindolinyl, dihydrobenzofuranylmethyl, morpholinylmethyl, morpholinylethyl, phenyl, nitrophenyl, methylphenyl, ethylphenyl, cyanomethylphenyl, morpholinylphenyl, pyrazolylphenyl, imidazolylphenyl, methoxyphenyl, difluoromethoxyphenyl, trifluoromethoxyphenyl, morpholinylethoxy-phenyl, ethylenedioxyphenyl, difluoromethylenedioxyphenyl, benzoyloxyphenyl, dimethylaminophenyl, acetylaminophenyl, aminocarbonylphenyl, (chloro)(methyl)-phenyl, dimethylphenyl, (methyl)(trifluoromethyl)phenyl, bis(trifluoromethyl)phenyl, (fluoropyrrolidinyl)(methyl)phenyl, (methyl)(pyrrolidinylmethyl)phenyl, (methyl)-(morpholinylmethyl)phenyl, (methyl)(methylpiperazinylmethyl)phenyl, (fluoro)-(methoxy)phenyl, (chloro)(methoxy)phenyl, (cyano)(methoxy)phenyl, (methoxy)-(methyl)phenyl, (methoxy)(trifluoromethyl)phenyl, dimethoxyphenyl, (difluoromethoxy)-(methyl)phenyl, (methyl)(trifluoromethoxy)phenyl, (methyl)(oxetanyloxy)phenyl, (azetidinyloxy)(methyl)phenyl, (tert-butoxycarbonylazetidinyloxy)(methyl)phenyl, (methyl)(tetrahydrofuranylmethoxy)phenyl, (methyl)(morpholinylethoxy)phenyl, (dimethylaminomethyl)(methyl)phenyl, trimethoxyphenyl, benzyl, cyanobenzyl, methylbenzyl, methoxybenzyl, methylenedioxybenzyl, dimethylaminobenzyl, dimethoxy-benzyl, phenylethyl, fluorophenylethyl, methylphenylethyl, (hydroxy)(phenyl)ethyl, methoxyphenylethyl, methylfuryl, methoxybenzofuryl, thienyl, indolyl, methylindolyl, pyrazolyl, methylpyrazolyl, dimethylpyrazolyl, indazolyl, methylindazolyl, dimethyl-isoxazolyl, thiazolyl, methylthiazolyl, tert-butylthiazolyl, ethoxycarbonylthiazolyl, benzothiazolyl, methoxybenzothiazolyl, methylimidazolyl, benzimidazolyl, methyl-benzimidazolyl, trifluoromethylbenzimidazolyl, piperidinylmethylbenzimidazolyl, morpholinylmethylbenzimidazolyl, imidazo[1,2-a]pyridinyl, benzothiadiazolyl, pyridinyl, chloropyridinyl, methylpiperazinylpyridinyl, methoxypyridinyl, dimethylpyridinyl, (methyl)(trifluoromethyl)pyridinyl, (azetidinyl)(methyl)pyridinyl, (methyl)(pyrrolidinyl)-pyridinyl, (methyl)(piperazinyl)pyridinyl, (fluoroazetidinyl)(methyl)pyridinyl, (fluoropyrrolidinyl)(methyl)pyridinyl, (methyl)(methylpiperazinyl)pyridinyl, (tert-butoxycarbonylpiperazinyl)(methyl)pyridinyl, (difluoroazetidinyl)(methyl)pyridinyl, (difluoropyrrolidinyl)(methyl)pyridinyl, (difluoropiperidinyl)(methyl)pyridinyl, (methyl)-(pyrrolidinylmethyl)pyridinyl, (methyl)(morpholinylmethyl)pyridinyl, (methyl)(methylpiperazinylmethyl)pyridinyl, (hydroxy)(methyl)pyridinyl, (dimethyl)(oxo)pyridinyl, (chloro)(methoxy)pyridinyl, (methoxy)(methyl)pyridinyl, (methoxy)(trifluoromethyl)-pyridinyl, dimethoxypyridinyl, (ethoxy)(methyl)pyridinyl, (isopropoxy)(methyl)pyridinyl, (difluoromethoxy)(methyl)pyridinyl, (methyl)(trifluoroethoxy)pyridinyl, (methyl)-(tetrahydrofuranyloxy)pyridinyl, (methyl)(pyrrolidinyloxy)pyridinyl, (tert-butoxy-carbonylazetidinyloxy)(methyl)pyridinyl, (tert-butoxycarbonylpyrrolidinyloxy)(methyl)-pyridinyl, (methyl)(methylamino)pyridinyl, (dimethylamino)(methyl)pyridinyl, quinolinyl, isoquinolinyl, methoxypyridazinyl, pyrimidinyl, (difluoroazetidinyl)(methyl)-pyrimidinyl, methoxypyrimidinyl, (methoxy)(methyl)pyrimidinyl, (dimethylamino)-(methyl)pyrimidinyl, pyrazinyl, methoxypyrazinyl, (methoxy)(methyl)pyrazinyl, quinoxalinyl, indolylmethyl, thiazolylmethyl, methylthiazolylmethyl, imidazo[2,1-b]-thiazolylmethyl, pyridinylmethyl, furylethyl, benzimidazolylethyl and pyridinylethyl. Additional values include (isopropoxy)(methyl)phenyl, (bromo)(methoxy)pyridinyl, (cyano)(methoxy)pyridinyl and (dimethylamino)(methyl)pyrazinyl.

Representative values of Z include (methoxy)(methyl)phenyl, (isopropoxy)(methyl)phenyl, (difluoromethoxy)(methyl)phenyl, (methyl)-(trifluoromethoxy)phenyl, imidazo[1,2-a]pyridinyl, (difluoroazetidinyl)(methyl)pyridinyl, (chloro)(methoxy)pyridinyl, (bromo)(methoxy)pyridinyl, (cyano)(methoxy)pyridinyl, (methoxy)(methyl)pyridinyl, (methoxy)(trifluoromethyl)pyridinyl, dimethoxypyridinyl, (ethoxy)(methyl)pyridinyl, (isopropoxy)(methyl)pyridinyl, (difluoromethoxy)(methyl)-pyridinyl, (dimethylamino)(methyl)pyridinyl and (dimethylamino)(methyl)pyrazinyl.

Typical values of Z include (methoxy)(methyl)phenyl, (difluoromethoxy)-(methyl)phenyl, (methyl)(trifluoromethoxy)phenyl, imidazo[1,2-a]pyridinyl, (difluoro-azetidinyl)(methyl)pyridinyl, (methoxy)(methyl)pyridinyl, (ethoxy)(methyl)pyridinyl, (isopropoxy)(methyl)pyridinyl and (difluoromethoxy)(methyl)pyridinyl.

In a first embodiment, Z represents (methoxy)(methyl)phenyl. In a first aspect of that embodiment, Z represents 4-methoxy-2-methylphenyl. In a second aspect of that embodiment, Z represents 4-methoxy-3-methylphenyl.

In a second embodiment, Z represents (difluoromethoxy)(methyl)phenyl, especially 4-(difluoromethoxy)-2-methylphenyl.

In a third embodiment, Z represents (methyl)(trifluoromethoxy)phenyl, especially 2-methyl-4-(trifluoromethoxy)phenyl.

In a fourth embodiment, Z represents imidazo[1,2-a]pyridinyl, especially imidazo-[1,2-a]pyridin-8-yl.

In a fifth embodiment, Z represents (difluoroazetidinyl)(methyl)pyridinyl, especially 6-(3,3-difluoroazetidin-1-yl)-2-methylpyridin-3-yl.

In a sixth embodiment, Z represents (methoxy)(methyl)pyridinyl. In a first aspect of that embodiment, Z represents 6-methoxy-2-methylpyridin-3-yl. In a second aspect of that embodiment, Z represents 6-methoxy-5-methylpyridin-3-yl.

In a seventh embodiment, Z represents dimethoxypyridinyl, especially 2,6-dimethoxypyridin-3-yl.

In an eighth embodiment, Z represents (ethoxy)(methyl)pyridinyl, especially 6-ethoxy-2-methylpyridin-3-yl.

In a ninth embodiment, Z represents (isopropoxy)(methyl)pyridinyl, especially 6-isopropoxy-2-methylpyridin-3-yl.

In a tenth embodiment, Z represents (difluoromethoxy)(methyl)pyridinyl, especially 6-(difluoromethoxy)-2-methylpyridin-3-yl.

In an eleventh embodiment, Z represents (isopropoxy)(methyl)phenyl, especially 4-isopropoxy-2-methylphenyl.

In a twelfth embodiment, Z represents (chloro)(methoxy)pyridinyl, especially 6-chloro-5-methoxypyridin-2-yl.

In a thirteenth embodiment, Z represents (bromo)(methoxy)pyridinyl, especially 6-bromo-5-methoxypyridin-2-yl.

In a fourteenth embodiment, Z represents (cyano)(methoxy)pyridinyl, especially 6-cyano-5-methoxypyridin-2-yl.

In a fifteenth embodiment, Z represents (methoxy)(trifluoromethyl)pyridinyl, especially 5-methoxy-6-(trifluoromethyl)pyridin-2-yl.

In an sixteenth embodiment, Z represents (dimethylamino)(methyl)pyridinyl, especially 6-(dimethylamino)-2-methylpyridin-3-yl.

In an seventeenth embodiment, Z represents (dimethylamino)(methyl)pyrazinyl, especially 5-(dimethylamino)-3-methylpyrazin-2-yl.

Generally, $A^1$ represents hydrogen, cyano or trifluoromethyl; or $A^1$ represents $C_{1-6}$ alkyl, optionally substituted by one or more substituents independently selected from —$OR^a$, —$NR^bR^c$, —$CO_2R^d$ and —$CONR^bR^c$; or $A^1$ represents $C_{3-7}$ cycloalkyl.

Typically, $A^1$ represents hydrogen or cyano; or $A^1$ represents $C_{1-6}$ alkyl, optionally substituted by one or more substituents independently selected from —$OR^a$, —$CO_2R^d$ and —$CONR^bR^c$; or $A^1$ represents $C_{3-7}$ cycloalkyl.

Suitably, $A^1$ represents $C_{1-6}$ alkyl, optionally substituted by —$OR^a$.

In a first embodiment, $A^1$ represents hydrogen. In a second embodiment, $A^1$ represents cyano. In a third embodiment, $A^1$ represents trifluoromethyl. In a fourth embodiment, $A^1$ represents $C_{1-6}$ alkyl, optionally substituted by one or more substituents independently selected from fluoro, —$OR^a$, trifluoromethoxy, —$NR^bR^c$, —$CO_2R^d$ and —$CONR^bR^c$. In a first aspect of that embodiment, $A^1$ represents $C_{1-6}$ alkyl, optionally substituted by one or more substituents independently selected from —$OR^a$, —$NR^bR^c$, —$CO_2R^d$ and —$CONR^bR^c$. In a second aspect of that embodiment, $A^1$ represents $C_{1-6}$ alkyl, optionally substituted by one or more substituents independently selected from —$OR^a$, —$CO_2R^d$ and —$CONR^bR^c$. In a third aspect of that embodiment, $A^1$ represents $C_{1-6}$ alkyl, optionally substituted by one or more substituents independently selected from —$OR^a$ and —$NR^bR^c$. In a fourth aspect of that embodiment, $A^1$ represents unsubstituted $C_{1-6}$ alkyl, typically methyl, ethyl, isopropyl or isobutyl, especially methyl or ethyl. In a fifth aspect of that embodiment, $A^1$ represents $C_{1-6}$ alkyl monosubstituted by —$OR^a$, —$CO_2R^d$ or —$CONR^bR^c$. In a sixth aspect of that embodiment, $A^1$ represents $C_{1-6}$ alkyl monosubstituted by —$OR^a$ or —$NR^bR^c$. In a seventh aspect of that embodiment, $A^1$ represents $C_{1-6}$ alkyl monosubstituted by —$OR^a$, especially hydroxyethyl. In an eighth aspect of that embodiment, $A^1$ represents $C_{1-6}$ alkyl disubstituted by two substituents independently selected from —$OR^a$ and —$NR^bR^c$. In a fifth embodiment, $A^1$ represents $C_{3-7}$ cycloalkyl, especially cyclopropyl.

Selected values of $A^1$ include hydrogen, cyano, methyl, ethyl, isopropyl, isobutyl, —$CH_2OR^a$, —$CH_2CH_2OR^a$, —$CH_2CO_2R^d$, —$CH_2CONR^bR^c$ and cyclopropyl.

Illustrative values of $A^1$ include methyl, ethyl and —$CH_2CH_2OR^a$.

Particular values of $A^1$ include methyl, ethyl and hydroxyethyl.

A first particular value of $A^1$ is methyl.

A second particular value of $A^1$ is ethyl.

A third particular value of $A^1$ is hydroxyethyl, especially 2-hydroxyethyl.

In a particular embodiment, $A^2$ represents hydrogen. In another embodiment, $A^2$ represents $C_{1-6}$ alkyl, especially methyl.

Selected values of $A^2$ include hydrogen and methyl.

Suitably, $R^1$ represents hydrogen, halogen, cyano, nitro, hydroxy, trifluoromethyl, trifluoromethoxy, —$OR^a$, —$SO_2R^a$, —$NR^bR^c$, —$CH_2NR^bR^c$, —$NR^cCOR^d$, —$CH_2NR^cCOR^d$, —$NR^cCO_2R^d$, —$NHCONR^bR^c$, —$NR^cSO_2R^e$, —$NHSO_2NR^bR^c$, —$COR^d$, —$CO_2R^d$, —$CONR^bR^c$, —$CON(OR^a)R^b$ or —$SO_2NR^bR^c$; or $R^1$ represents $C_{1-6}$ alkyl, aryl or heteroaryl, any of which groups may be optionally substituted by one or more substituents.

Typically, $R^1$ represents hydrogen, —$NR^bR^c$ or —$NR^c$-$COR^d$; or $R^1$ represents $C_{1-6}$ alkyl, which group may be optionally substituted by one or more substituents.

Suitable values of $R^1$ include hydrogen and —$NR^bR^c$.

In a first embodiment, $R^1$ represents hydrogen. In a second embodiment, $R^1$ represents cyano. In a third embodiment, $R^1$ represents —$OR^a$. In a fourth embodiment, $R^1$ represents —$SR^a$. In a fifth embodiment, $R^1$ represents —$SO_2R^a$. In a sixth embodiment, $R^1$ represents —$NR^bR^c$. In a seventh embodiment, $R^1$ represents —$NR^cCOR^d$. In an eighth embodiment, $R^1$ represents optionally substituted $C_{1-6}$ alkyl. In one aspect of that embodiment, $R^1$ represents optionally substituted methyl.

Examples of typical substituents on $R^1$ include one or more substituents independently selected from halogen, cyano, nitro, $C_{1-6}$ alkyl, trifluoromethyl, aryl($C_{1-6}$)alkyl, hydroxy, $C_{1-6}$ alkoxy, difluoromethoxy, trifluoromethoxy, aryloxy, $C_{1-4}$ alkylenedioxy, $C_{1-6}$ alkoxy($C_{1-6}$)alkyl, $C_{1-6}$ alkylthio, $C_{1-6}$ alkylsulphonyl, oxo, amino, $C_{1-6}$ alkylamino, di($C_{1-6}$)alkylamino, $C_{2-6}$ alkylcarbonylamino, $C_{2-6}$ alkoxycarbonylamino, aryl($C_{1-6}$)alkoxycarbonylamino, $C_{1-6}$ alkylaminocarbonylamino, arylaminocarbonylamino, $C_{1-6}$ alkylsulphonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulphonyl, $C_{1-6}$ alkylaminosulphonyl and di($C_{1-6}$)alkylaminosulphonyl.

Specific examples of typical substituents on $R^1$ include one or more substituents independently selected from fluoro, chloro, bromo, cyano, nitro, methyl, ethyl, tert-butyl, trifluoromethyl, benzyl, hydroxy, methoxy, difluoromethoxy, trifluoromethoxy, phenoxy, methylenedioxy, ethylenedioxy, methoxymethyl, methylthio, methylsulphonyl, oxo, amino, methylamino, dimethylamino, acetylamino, methoxycarbonylamino, ethoxycarbonylamino, benzyloxycarbonylamino, ethylaminocarbonylamino, butylaminocarbonylamino, phenylaminocarbonylamino, methylsulphonylamino, formyl, acetyl, carboxy, methoxycarbonyl, aminocarbonyl, methylaminocarbonyl, dimethylaminocarbonyl, aminosulphonyl, methylaminosulphonyl and dimethylaminosulphonyl.

Generally, $R^2$ represents hydrogen, cyano, hydroxy, trifluoromethyl, —$NR^cCO_2R^d$, —$COR^d$, —$CO_2R^d$, —$CONR^bR^c$ or —$CON(OR^a)R^b$; or $C_{1-6}$ alkyl, $C_{3-7}$ cycloalkyl, aryl, $C_{3-7}$ heterocycloalkyl, $C_{3-7}$ heterocycloalkenyl or heteroaryl, any of which groups may be optionally substituted by one or more substituents.

In a first embodiment, $R^2$ represents hydrogen. In a second embodiment, $R^2$ represents cyano. In a third embodiment, $R^2$ represents hydroxy. In a fourth embodiment, $R^2$ represents trifluoromethyl. In a fifth embodiment, $R^2$ represents —$NR^cCO_2R^d$. In a sixth embodiment, $R^2$ represents —$COR^d$. In a seventh embodiment, $R^2$ represents —$CO_2R^d$. In an eighth embodiment, $R^2$ represents —$CONR^bR^c$. In a ninth embodiment, $R^2$ represents —$CON(OR^a)R^b$. In a tenth embodiment, $R^2$ represents optionally substituted $C_{1-6}$ alkyl. In a first aspect of that embodiment, $R^2$ represents unsubstituted $C_{1-6}$ alkyl. In a second aspect of that embodiment, $R^2$ represents monosubstituted $C_{1-6}$ alkyl. In a third aspect of that embodiment, $R^2$ represents disubstituted $C_{1-6}$ alkyl. In an eleventh embodiment, $R^2$ represents optionally substituted $C_{3-7}$ cycloalkyl. In a first aspect of that embodiment, $R^2$ represents unsubstituted $C_{3-7}$ cycloalkyl. In a second aspect of that embodiment, $R^2$ represents monosubstituted $C_{3-7}$ cycloalkyl. In a third aspect of that embodiment, $R^2$ represents disubstituted $C_{3-7}$ cycloalkyl. In a twelfth embodiment, $R^2$ represents optionally substituted aryl. In a first aspect of that embodiment, $R^2$ represents unsubstituted aryl. In a second aspect of that embodiment, $R^2$ represents monosubstituted aryl. In a third aspect of that embodiment, $R^2$ represents disubstituted aryl. In a thirteenth embodiment, $R^2$ represents optionally substituted $C_{3-7}$ heterocycloalkyl. In a first aspect of that embodiment, $R^2$ represents unsubstituted $C_{3-7}$ heterocycloalkyl. In a second aspect of that embodiment, $R^2$ represents monosubstituted $C_{3-7}$ heterocycloalkyl. In a third aspect of that embodiment, $R^2$ represents disubstituted $C_{3-7}$ heterocycloalkyl. In a fourteenth embodiment, $R^2$ represents optionally substituted $C_{3-7}$ heterocycloalkenyl. In a first aspect of that embodiment, $R^2$ represents unsubstituted $C_{3-7}$ heterocycloalkenyl. In a second aspect of that embodiment, $R^2$ represents monosubstituted $C_{3-7}$ heterocycloalkenyl. In a third aspect of that embodiment, $R^2$ represents disubstituted $C_{3-7}$ heterocycloalkenyl. In a fifteenth embodiment, $R^2$ represents optionally substituted heteroaryl. In a first aspect of that embodiment, $R^2$ represents unsubstituted heteroaryl. In a second aspect of that embodiment, $R^2$ represents monosubstituted heteroaryl. In a third aspect of that embodiment, $R^2$ represents disubstituted heteroaryl.

Where $R^2$ represents optionally substituted $C_{1-6}$ alkyl, suitable values include methyl, ethyl, n-propyl, isopropyl, n-butyl, isobutyl and tert-butyl, any of which groups may be optionally substituted by one or more substituents. Selected values include methyl, hydroxymethyl, chloropropyl and isobutyl. Particular values include methyl and isobutyl, especially methyl.

Where $R^2$ represents optionally substituted $C_{3-7}$ cycloalkyl, a suitable value is cyclohexyl, optionally substituted by one or more substituents.

Where $R^2$ represents optionally substituted aryl, a suitable value is phenyl, optionally substituted by one or more substituents. Selected values include phenyl, fluorophenyl, chlorophenyl and methoxyphenyl.

Where $R^2$ represents optionally substituted $C_{3-7}$ heterocycloalkyl, typical values include azetidinyl, pyrrolidinyl, piperidinyl, piperazinyl, morpholinyl and thiomorpholinyl, any of which groups may be optionally substituted by one or more substituents.

Where $R^2$ represents optionally substituted $C_{3-7}$ heterocycloalkenyl, a typical value is oxazolinyl, optionally substituted by one or more substituents. Suitable values include oxazolinyl, methyloxazolinyl, isopropyloxazolinyl and dimethyloxazolinyl.

Where $R^2$ represents optionally substituted heteroaryl, typical values include pyrrolyl, furyl, thienyl, imidazolyl, oxazolyl, isoxazolyl, thiazolyl, isothiazolyl, pyrazolyl, triazolyl, oxadiazolyl, thiadiazolyl, pyridinyl, pyrimidinyl, pyridazinyl, pyrazinyl, tetrazolyl and triazinyl, any of which groups may be optionally substituted by one or more substituents. Suitable values include oxadiazolyl and pyridinyl, either of which groups may be optionally substituted by one or more substituents. Selected values include methyloxadiazolyl, isopropyloxadiazolyl, tert-butyloxadiazolyl and pyridinyl.

In a selected embodiment, $R^2$ represents hydrogen, cyano, hydroxy, trifluoromethyl, —$NR^cCO_2R^d$, —$COR^d$, —$CO_2R^d$, —$CONR^bR^c$ or —$CON(OR^a)R^b$; or $R^2$ represents $C_{1-6}$ alkyl, cyclohexyl, phenyl, oxazolinyl, oxadiazolyl or pyridinyl, any of which groups may be optionally substituted by one or more substituents.

Typical examples of optional substituents on $R^2$ include one or more substituents independently selected from halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$) alkylaminosulfonyl.

Typical examples of specific substituents on $R^2$ include one or more substituents independently selected from fluoro, chloro, bromo, cyano, nitro, methyl, ethyl, isopropyl, tert-butyl, trifluoromethyl, hydroxy, methoxy, isopropoxy, difluoromethoxy, trifluoro-methoxy, methylthio, methylsulfinyl, methylsulfonyl, amino, methylamino, dimethylamino, acetylamino, methoxycarbonylamino, methylsulfonylamino, formyl, acetyl, carboxy, methoxycarbonyl, aminocarbonyl, methylaminocarbonyl, dimethylaminocarbonyl, aminosulfonyl, methylaminosulfonyl and dimethylaminosulfonyl.

Typical values of $R^2$ include hydrogen, cyano, hydroxy, trifluoromethyl, —$NR^cCO_2R^d$, —$COR^d$, —$CO_2R^d$, —$CONR^bR^c$, —$CON(OR^a)R^b$, methyl, hydroxymethyl, chloropropyl, isobutyl, cyclohexyl, phenyl, fluorophenyl, chlorophenyl, methoxyphenyl, oxazolinyl, methyloxazolinyl, isopropyloxazolinyl, dimethyloxazolinyl, methyloxadiazolyl, isopropyloxadiazolyl, tert-butyloxadiazolyl and pyridinyl.

Typically, $R^2$ represents hydrogen, trifluoromethyl or $C_{1-6}$ alkyl.

Illustrative values of $R^2$ include hydrogen, trifluoromethyl and methyl.

Suitably, $R^2$ represents hydrogen.

Generally, $R^3$ represents hydrogen; or $R^3$ represents $C_{1-6}$ alkyl, optionally substituted by one or two halogen atoms.

Typically, $R^3$ represents hydrogen or $C_{1-6}$ alkyl.

Suitable values of $R^3$ include hydrogen and methyl.

In one embodiment, $R^3$ represents hydrogen. In another embodiment, $R^3$ represents $C_{1-6}$ alkyl, especially methyl.

Suitably, $R^4$ represents hydrogen or $C_{1-6}$ alkyl.

Suitable values of $R^4$ include hydrogen and methyl.

In one embodiment, $R^4$ represents hydrogen. In another embodiment, $R^4$ represents $C_{1-6}$ alkyl, optionally substituted by one or more substituents independently selected from —$OR^a$ and —$NR^bR^c$. In one aspect of that embodiment, $R^4$ represents unsubstituted $C_{1-6}$ alkyl, especially methyl. In another aspect of that embodiment, $R^4$ represents $C_{1-6}$ alkyl monosubstituted by —$OR^a$ or —$NR^bR^c$. In a further aspect of that embodiment, $R^4$ represents $C_{1-6}$ alkyl disubstituted by two substituents independently selected from —$OR^a$ and —$NR^bR^c$.

Typical examples of suitable substituents on $R^a$, $R^b$, $R^c$, $R^d$ or $R^e$, or on the heterocyclic moiety —$NR^bR^c$, include halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphinyl, $C_{1-6}$ alkylsulphonyl, hydroxy, hydroxy($C_{1-6}$) alkyl, amino($C_{1-6}$)alkyl, cyano, trifluoromethyl, oxo, $C_{2-6}$ alkylcarbonyl, carboxy, $C_{2-6}$ alkoxycarbonyl, $C_{2-6}$ alkylcarbonyloxy, amino, $C_{1-6}$ alkylamino, di($C_{1-6}$)alkylamino, phenylamino, pyridinylamino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulphonylamino, aminocarbonyl, $C_{1-6}$ alkylaminocarbonyl and di($C_{1-6}$)alkylaminocarbonyl.

Typical examples of specific substituents on $R^a$, $R^b$, $R^c$, $R^d$ or $R^e$, or on the heterocyclic moiety —$NR^bR^c$, include fluoro, chloro, bromo, methyl, ethyl, isopropyl, methoxy, isopropoxy, difluoromethoxy, trifluoromethoxy, methoxymethyl, methylthio, ethylthio, methylsulphinyl, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, acetoxy, amino, methylamino, ethylamino, dimethylamino, phenylamino, pyridinylamino, acetylamino, acetylaminomethyl, tert-butoxycarbonylamino, methylsulphonylamino, aminocarbonyl, methylaminocarbonyl and dimethylaminocarbonyl.

Typically, $R^a$ represents hydrogen; or $R^a$ represents $C_{1-6}$ alkyl, aryl($C_{1-6}$)alkyl or heteroaryl($C_{1-6}$)alkyl, any of which groups may be optionally substituted by one or more substituents.

Suitably, $R^a$ represents $C_{1-6}$ alkyl, aryl($C_{1-6}$)alkyl or heteroaryl($C_{1-6}$)alkyl, any of which groups may be optionally substituted by one or more substituents.

Apposite values of $R^a$ include hydrogen; and methyl, ethyl, benzyl or isoindolylpropyl, any of which groups may be optionally substituted by one or more substituents.

Selected values of $R^a$ include methyl, ethyl, benzyl and isoindolylpropyl, any of which groups may be optionally substituted by one or more substituents.

Selected examples of suitable substituents on $R^a$ include $C_{1-6}$ alkoxy and oxo.

Selected examples of specific substituents on $R^a$ include methoxy and oxo.

In one embodiment, $R^a$ represents hydrogen. In another embodiment, $R^a$ represents optionally substituted $C_{1-6}$ alkyl. In one aspect of that embodiment, $R^a$ ideally represents unsubstituted $C_{1-6}$ alkyl, especially methyl. In another aspect of that embodiment, $R^a$ ideally represents substituted $C_{1-6}$ alkyl, e.g. methoxyethyl. In another embodiment, $R^a$ represents optionally substituted aryl. In one aspect of that embodiment, $R^a$ represents unsubstituted aryl, especially phenyl. In another aspect of that embodiment, $R^a$ represents monosubstituted aryl, especially methylphenyl. In another embodiment, $R^a$ represents optionally substituted aryl($C_{1-6}$) alkyl, ideally unsubstituted aryl($C_{1-6}$)alkyl, especially benzyl. In a further embodiment, $R^a$ represents optionally substituted heteroaryl. In a further embodiment, $R^a$ represents optionally substituted heteroaryl($C_{1-6}$)alkyl, e.g. dioxoisoindolylpropyl.

Specific values of $R^a$ include methyl, methoxyethyl, benzyl and dioxoisoindolylpropyl.

Appositely, $R^a$ represents hydrogen or $C_{1-6}$ alkyl.

Individual values of $R^a$ include hydrogen and methyl.

In a particular aspect, $R^b$ represents hydrogen or trifluoromethyl; or $C_{1-6}$ alkyl, $C_{3-7}$ cycloalkyl, $C_{3-7}$ cycloalkyl ($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$) alkyl, any of which groups may be optionally substituted by one or more substituents.

Selected values of $R^b$ include hydrogen; or $C_{1-6}$ alkyl, aryl($C_{1-6}$)alkyl, $C_{3-7}$ heterocycloalkyl or $C_{3-7}$ heterocycloalkyl($C_{1-6}$)alkyl, any of which groups may be optionally substituted by one or more substituents.

Typical values of $R^b$ include hydrogen and $C_{1-6}$ alkyl.

Illustratively, $R^b$ represents hydrogen or trifluoromethyl; or methyl, ethyl, n-propyl, isopropyl, n-butyl, 2-methylpropyl, tert-butyl, pentyl, hexyl, cyclopropyl, cyclobutyl, cyclopentyl, cyclohexyl, cyclopropylmethyl, cyclobutylmethyl, cyclopentylmethyl, cyclohexylmethyl, phenyl, benzyl, phenylethyl, azetidinyl, tetrahydrofuryl, tetrahydrothienyl, pyrrolidinyl, piperidinyl, homopiperidinyl, morpholinyl, azetidinylmethyl, tetrahydrofurylmethyl, pyrrolidinylmethyl, pyrrolidinylethyl, pyrrolidinylpropyl, thiazolidinylmethyl, imidazolidinylethyl, piperidinylmethyl, piperidinylethyl, tetrahydroquinolinylmethyl, pip erazinylpropyl, morpholinylmethyl, morpholinylethyl, morpholinylpropyl, pyridinyl, indolylmethyl, pyrazolylmethyl, pyrazolylethyl, imidazolylmethyl, imidazolylethyl, benzimidazolylmethyl, triazolylmethyl, pyridinylmethyl or pyridinylethyl, any of which groups may be optionally substituted by one or more substituents.

Representative values of $R^b$ include hydrogen; or methyl, ethyl, n-propyl, benzyl, pyrrolidinyl or morpholinylpropyl, any of which groups may be optionally substituted by one or more substituents.

Selected examples of suitable substituents on $R^b$ include $C_{1-6}$ alkoxy, $C_{1-6}$ alkylthio, $C_{1-6}$ alkylsulphinyl, $C_{1-6}$ alkylsulphonyl, hydroxy, cyano, $C_{2-6}$ alkoxycarbonyl, di-($C_{1-6}$) alkylamino and $C_{2-6}$ alkoxycarbonylamino.

Selected examples of specific substituents on $R^b$ include methoxy, methylthio, methylsulphinyl, methylsulphonyl, hydroxy, cyano, tert-butoxycarbonyl, dimethylamino and tert-butoxycarbonylamino.

Specific values of $R^b$ include hydrogen, methyl, methoxyethyl, methylthioethyl, methylsulphinylethyl, methylsulphonylethyl, hydroxyethyl, cyanoethyl, dimethylamino-ethyl, tert-butoxycarbonylaminoethyl, dihydroxypropyl, benzyl, pyrrolidinyl, tert-butoxycarbonylpyrrolidinyl and morpholinylpropyl.

In one embodiment, $R^b$ represents hydrogen. In another embodiment, $R^b$ represents $C_{1-6}$ alkyl, especially methyl.

Selected values of $R^c$ include hydrogen; or $C_{1-6}$ alkyl, $C_{3-7}$ cycloalkyl or $C_{3-7}$ heterocycloalkyl, any of which groups may be optionally substituted by one or more substituents.

In a particular aspect, $R^c$ represents hydrogen, $C_{1-6}$ alkyl or $C_{3-7}$ cycloalkyl.

Representative values of $R^c$ include hydrogen; or methyl, cyclobutyl, cyclopentyl, cyclohexyl, tetrahydropyranyl and piperidinyl, any of which groups may be optionally substituted by one or more substituents.

Selected examples of suitable substituents on $R^c$ include $C_{2-6}$ alkylcarbonyl and $C_{2-6}$ alkoxycarbonyl.

Selected examples of specific substituents on $R^c$ include acetyl and tert-butoxycarbonyl.

Specific values of $R^c$ include hydrogen, methyl, cyclobutyl, cyclopentyl, cyclohexyl, tetrahydropyranyl, acetylpiperidinyl and tert-butoxycarbonylpiperidinyl.

Suitably, $R^c$ represents hydrogen or $C_{1-6}$ alkyl. In one embodiment, $R^c$ is hydrogen. In another embodiment, $R^c$ represents $C_{1-6}$ alkyl, especially methyl or ethyl, particularly methyl. In a further embodiment, $R^c$ represents $C_{3-7}$ cycloalkyl, e.g. cyclopropyl, cyclobutyl, cyclopentyl or cyclohexyl.

Alternatively, the moiety —$NR^bR^c$ may suitably represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents.

Selected examples of suitable substituents on the heterocyclic moiety —$NR^bR^c$ include $C_{1-6}$ alkyl, $C_{1-6}$ alkylsulphonyl, hydroxy, hydroxy($C_{1-6}$)alkyl, amino($C_{1-6}$)alkyl, cyano, oxo, $C_{2-6}$ alkylcarbonyl, carboxy, $C_{2-6}$ alkoxycarbonyl, amino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulphonylamino and aminocarbonyl.

Selected examples of specific substituents on the heterocyclic moiety —$NR^bR^c$ include methyl, methylsulphonyl, hydroxy, hydroxymethyl, aminomethyl, cyano, oxo, acetyl, carboxy, ethoxycarbonyl, amino, acetylamino, acetylaminomethyl, tert-butoxycarbonylamino, methylsulphonylamino and aminocarbonyl.

Specific values of the moiety —$NR^bR^c$ include azetidin-1-yl, hydroxyazetidin-1-yl, hydroxymethylazetidin-1-yl, (hydroxy)(hydroxymethyl)azetidin-1-yl, aminomethyl-azetidin-1-yl, cyanoazetidin-1-yl, carboxyazetidin-1-yl, aminoazetidin-1-yl, aminocarbonylazetidin-1-yl, pyrrolidin-1-yl, aminomethylpyrrolidin-1-yl, oxopyrrolidin-1-yl, acetylaminomethylpyrrolidin-1-yl, tert-butoxycarbonylaminopyrrolidin-1-yl, oxo-oxazolidin-3-yl, hydroxyisoxazolidin-2-yl, thiazolidin-3-yl, oxothiazolidin-3-yl, dioxo-isothiazolidin-2-yl, piperidin-1-yl, hydro xypiperidin-1-yl, hydroxymethylpiperidin-1-yl, aminopiperidin-1-yl, acetylaminopiperidin-1-yl, tert-butoxycarbonylaminopiperidin-1-yl, methylsulphonylaminopiperidin-1-yl, morpholin-4-yl, piperazin-1-yl, methylpiperazin-1-yl, methylsulphonylpiperazin-1-yl, oxopiperazin-1-yl, acetylpiperazin-1-yl, ethoxycarbonylpiperazin-1-yl and oxohomopiperazin-1-yl.

Suitably, $R^d$ represents hydrogen; or $C_{1-6}$ alkyl, aryl or heteroaryl, any of which groups may be optionally substituted by one or more substituents.

Selected examples of suitable values for $R^d$ include hydrogen, methyl, ethyl, isopropyl, 2-methylpropyl, tert-butyl, cyclopropyl, cyclobutyl, phenyl, thiazolidinyl, thienyl, imidazolyl and thiazolyl, any of which groups may be optionally substituted by one or more substituents.

Selected examples of suitable substituents on $R^d$ include halogen, $C_{1-6}$ alkyl, $C_{1-6}$ alkoxy, oxo, $C_{2-6}$ alkylcarbonyloxy and di($C_{1-6}$)alkylamino.

Selected examples of particular substituents on $R^d$ include fluoro, methyl, methoxy, oxo, acetoxy and dimethylamino.

In one embodiment, $R^d$ represents hydrogen. In another embodiment, $R^d$ represents optionally substituted $C_{1-6}$ alkyl. In one aspect of that embodiment, $R^d$ ideally represents unsubstituted $C_{1-6}$ alkyl, e.g. methyl, ethyl, isopropyl, 2-methylpropyl or tert-butyl, especially methyl or ethyl, particularly methyl. In another aspect of that embodiment, $R^d$ ideally represents substituted $C_{1-6}$ alkyl, e.g. substituted methyl or substituted ethyl, including acetoxymethyl, dimethylaminomethyl and trifluoroethyl. In another embodiment, $R^d$ represents optionally substituted aryl. In one aspect of that embodiment, $R^d$ represents unsubstituted aryl, especially phenyl. In another aspect of that embodiment, $R^d$ represents monosubstituted aryl, especially methylphenyl. In a further aspect of that embodiment, $R^d$ represents disubstituted aryl, e.g. dimethoxyphenyl. In a further embodiment, $R^d$ represents optionally substituted heteroaryl, e.g. thienyl, chlorothienyl, methylthienyl, methylimidazolyl or thiazolyl. In another embodiment, $R^d$ represents optionally substituted $C_{3-7}$ cycloalkyl, e.g. cyclopropyl or cyclobutyl. In a further embodiment, $R^d$ represents optionally substituted $C_{3-7}$ heterocycloalkyl, e.g. thiazolidinyl or oxothiazolidinyl.

Selected examples of specific values for $R^d$ include hydrogen, methyl, ethyl, acetoxymethyl, dimethylaminomethyl, ethyl, trifluoroethyl, isopropyl, 2-methylpropyl, tert-butyl, cyclopropyl, cyclobutyl, phenyl, dimethoxyphenyl, thiazolidinyl, oxothiazolidinyl, thienyl, chlorothienyl, methylthienyl, methylimidazolyl and thiazolyl.

Appositely, $R^d$ represents hydrogen or $C_{1-6}$ alkyl.

Individual values of $R^d$ include hydrogen and methyl.

A particular value of $R^d$ is ethyl.

Suitably, $R^e$ represents $C_{1-6}$ alkyl or aryl, either of which groups may be optionally substituted by one or more substituents.

Selected examples of suitable substituents on $R^e$ include $C_{1-6}$ alkyl, especially methyl.

In one embodiment, $R^e$ represents optionally substituted $C_{1-6}$ alkyl, ideally unsubstituted $C_{1-6}$ alkyl, e.g. methyl or propyl, especially methyl. In another embodiment, $R^e$ represents optionally substituted aryl. In one aspect of that embodiment, $R^e$ represents unsubstituted aryl, especially phenyl. In another aspect of that embodiment, $R^e$ represents monosubstituted aryl, especially methylphenyl. In a further embodiment, $R^e$ represents optionally substituted heteroaryl.

Selected values of $R^e$ include methyl, propyl and methylphenyl.

In a particular aspect, the present invention provides a compound of formula (IA), or a pharmaceutically acceptable salt or solvate thereof:

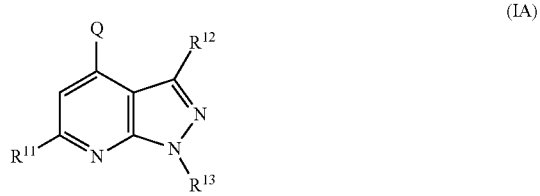

(IA)

wherein Q is as defined above;
$R^{11}$ represents hydrogen or amino;
$R^{12}$ represents hydrogen, trifluoromethyl or $C_{1-6}$ alkyl; and
$R^{13}$ represents hydrogen or $C_{1-6}$ alkyl.

In a first embodiment, $R^{11}$ is hydrogen. In a second embodiment, $R^{11}$ is $-NH_2$.

Suitably, $R^{12}$ represents hydrogen or $C_{1-6}$ alkyl.

Suitable values of $R^{12}$ include hydrogen, trifluoromethyl and methyl.

In a first embodiment, $R^{12}$ represents hydrogen. In a second embodiment, $R^{12}$ represents trifluoromethyl. In third embodiment, $R^{12}$ represents $C_{1-6}$ alkyl, especially methyl.

Suitable values of $R^{13}$ include hydrogen and methyl.

In one embodiment, $R^{13}$ represents hydrogen. In another embodiment, $R^{13}$ represents $C_{1-6}$ alkyl, especially methyl.

One sub-class of compounds according to the invention is represented by the compounds of formula (IIA), and pharmaceutically acceptable salts and solvates thereof:

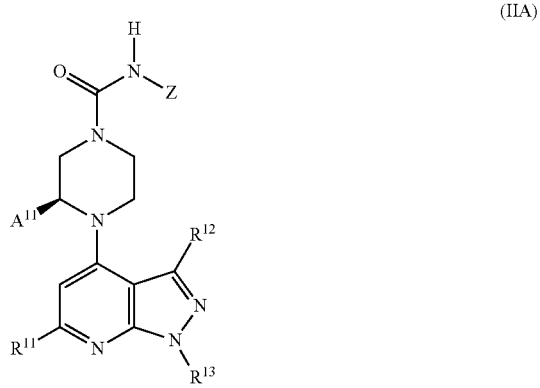

(IIA)

wherein
$A^{11}$ represents hydrogen, cyano, $C_{1-6}$ alkyl, $-CH_2OR^a$, $-CH_2CH_2OR^a$, $-CH_2CO_2R^d$, $-CH_2CONR^bR^c$ or $C_{3-7}$ cycloalkyl; and
Z, $R^{11}$, $R^{12}$, $R^{13}$, $R^a$, $R^b$, $R^c$ and $R^d$ are as defined above.

In a first embodiment, $A^{11}$ represents hydrogen. In a second embodiment, $A^{11}$ represents cyano. In a third embodiment, $A^{11}$ represents $C_{1-6}$ alkyl, typically methyl, ethyl, isopropyl or isobutyl, especially methyl or ethyl. In a fourth embodiment, $A^{11}$ represents $-CH_2OR^a$. In a fifth embodiment, $A^{11}$ represents $-CH_2CH_2OR^a$. In a sixth embodiment, $A^{11}$ represents $-CH_2CO_2R^d$. In a seventh embodiment, $A^{11}$ represents $-CH_2CONR^bR^c$. In an eighth embodiment, $A^{11}$ represents $C_{3-7}$ cycloalkyl, especially cyclopropyl.

Selected values of $A^{11}$ include hydrogen, cyano, methyl, ethyl, isopropyl, isobutyl, $-CH_2OR^a$, $-CH_2CH_2OR^a$, $-CH_2CO_2R^d$, $-CH_2CONR^bR^c$ and cyclopropyl.

Typically, $A^{11}$ represents $C_{1-6}$ alkyl or $-CH_2CH_2OR^a$.

Particular values of $A^{11}$ include methyl, ethyl and 2-hydroxyethyl.

A first particular value of $A^{11}$ is methyl.
A second particular value of $A^{11}$ is ethyl.
A third particular value of $A^{11}$ is 2-hydroxyethyl.

Another sub-class of compounds according to the invention is represented by the compounds of formula (IIB), and pharmaceutically acceptable salts and solvates thereof:

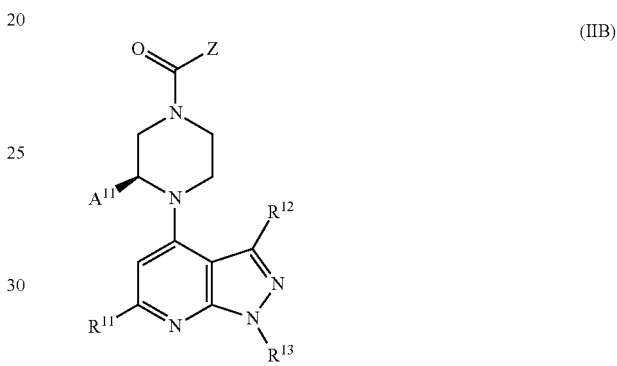

(IIB)

wherein Z, $A^{11}$, $R^{11}$, $R^{12}$ and $R^{13}$ are as defined above.

Specific novel compounds in accordance with the present invention include each of the compounds whose preparation is described in the accompanying Examples, and pharmaceutically acceptable salts and solvates thereof.

The compounds in accordance with the present invention are beneficial in the treatment and/or prevention of various human ailments. These include inflammatory, autoimmune and oncological disorders; viral diseases and malaria; and organ and cell transplant rejection.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, vasculitis, polymyositis, scleroderma, multiple sclerosis, ankylosing spondylitis, rheumatoid arthritis and Sjögren's syndrome. Autoimmune endocrine disorders include thyroiditis. Organ-specific autoimmune disorders include Addison's disease, haemolytic or pernicious anaemia, glomerulonephritis (including Goodpasture's syndrome), Graves' disease, idiopathic thrombocytopenic purpura, insulin-dependent diabetes mellitus, juvenile diabetes, uveitis, inflammatory bowel disease (including Crohn's disease and ulcerative colitis), pemphigus, atopic dermatitis, autoimmune hepatitis, primary biliary cirrhosis, autoimmune pneumonitis, autoimmune carditis, myasthenia gravis and spontaneous infertility.

Oncological disorders, which may be acute or chronic, include proliferative disorders, especially cancer, in animals, including mammals, especially humans. Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle.

Viral diseases include infections caused by various families of virus, including the Retroviridae, Flaviviridae, Picornaviridae. Various genera within the Retroviridae family include Alpharetrovirus, Betaretrovirus, Gammaretrovirus, Deltaretrovirus, Epsilonretrovirus, Lentivirus and Spumavirus. Members of the Lentivirus genus include human immunodeficiency virus 1 (HIV-1) and human immunodeficiency virus 2 (HIV-2). Various genera within the Flaviviridae family include Flavivirus, Pestivirus, Hepacivirus and Hepatitis G Virus. Members of the Flavivirus genus include Dengue fever virus, yellow fever virus, West Nile encephalitis virus and Japanese encephalitis virus. Members of the Pestivirus genus include bovine viral diarrhoea virus (BVDV), classical swine fever virus and border disease virus 2 (BDV-2). Members of the Hepacivirus genus include hepatitis C virus (HCV). Members of the Hepatitis G Virus genus include hepatitis G virus. Various genera within the Picornaviridae family include Aphthovirus, Avihepatovirus, Cardiovirus, Enterovirus, Erbovirus, Hepatovirus, Kobuvirus, Parechovirus, Sapelovirus, Senecavirus, Teschovirus and Tremovirus. Members of the Enterovirus genus include poliovirus, coxsackie A virus, coxsackie B virus and rhinovirus.

Organ transplant rejection includes the rejection of transplanted or grafted organs or cells (both allografts and xenografts), including graft-versus-host reaction disease. The term "organ" as used herein means all organs or parts of organs in mammals, particularly humans, including kidney, lung, bone marrow, hair, cornea, eye (vitreous), heart, heart valve, liver, pancreas, blood vessel, skin, muscle, bone, intestine and stomach. The term "rejection" as used herein means all reactions of the recipient body or the transplanted organ which ultimately lead to cell or tissue death in the transplanted organ, or adversely affect the functional ability and viability of the transplanted organ or the recipient. In particular, this means acute and chronic rejection reactions.

Cell transplant rejection includes the rejection of cell transplants and xenotransplantation. The major hurdle for xenotransplantation is that even before the T lymphocytes (responsible for the rejection of allografts) are activated, the innate immune system (especially T-independent B lymphocytes and macrophages) is activated. This provokes two types of severe and early acute rejection, referred to as hyperacute rejection and vascular rejection respectively. Conventional immunosuppressant drugs, including cyclosporine A, are ineffective in xenotransplantation. The compounds in accordance with the present invention are not liable to this drawback. The ability of the compounds of this invention to suppress T-independent xeno-antibody production as well as macrophage activation may be demonstrated by their ability to prevent xenograft rejection in athymic, T-deficient mice receiving xenogenic hamster-heart grafts.

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of formula (I) above may be prepared by a process which comprises reacting a compound of formula (III) with a compound of formula (IV):

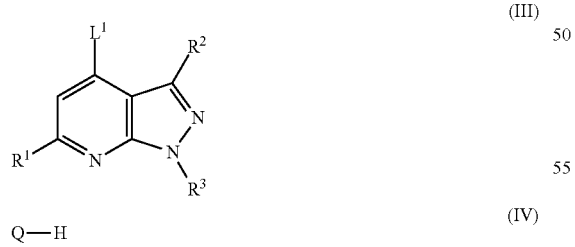

wherein Q, $R^1$, $R^2$ and $R^3$ are as defined above, and $L^1$ represents a suitable leaving group.

The leaving group $L^1$ is typically a halogen atom, e.g. chloro.

The reaction will generally be carried out in the presence of a base, typically an organic amine such as N,N-diisopropylethylamine. The reaction is conveniently effected at ambient or elevated temperature in a suitable solvent, e.g. a lower alkanol such as n-butanol, a cyclic ether solvent such as 1,4-dioxane, or a dipolar aprotic solvent such as N,N-dimethylformamide.

In another procedure, the compounds of formula (I) above wherein Y represents —C(O)—, —S(O)$_2$— or —C(O)O— may be prepared by a process which comprises reacting a compound of formula $L^2$-C(O)—Z, $L^2$-S(O)$_2$—Z or $L^2$-C(O)O—Z respectively with a compound of formula (VA), (VB), (VC), (VD) or (VE):

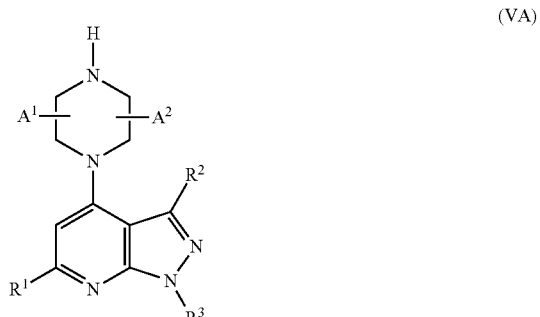

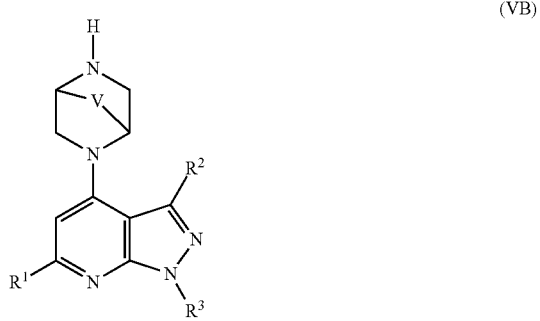

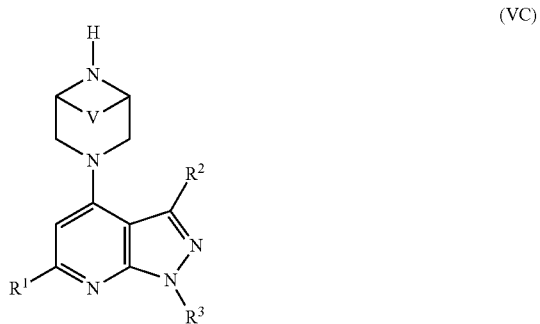

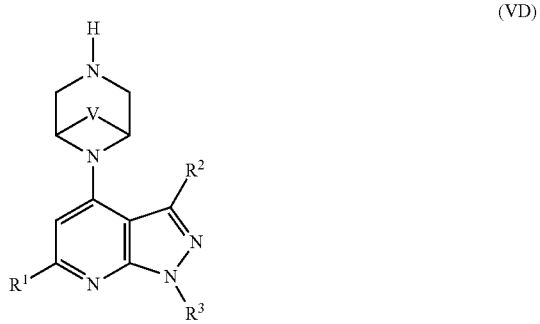

-continued

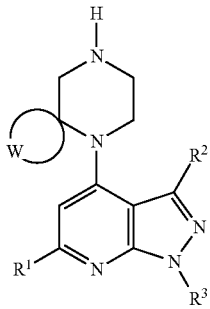

(VE)

wherein V, W, Z, $A^1$, $A^2$, $R^1$, $R^2$ and $R^3$ are as defined above, and $L^2$ represents a suitable leaving group.

The leaving group $L^2$ is typically a halogen atom, e.g. chloro.

The reaction is conveniently effected at ambient temperature in a suitable solvent, e.g. an ethereal solvent such as 1,4-dioxane, or a chlorinated solvent such as dichloromethane, typically in the presence of a base. A suitable base for use in the reaction may be an organic base such as N,N-diisopropylethylamine, or an inorganic base such as potassium carbonate.

Alternatively, the leaving group $L^2$ may be 2-methyl-3-(trifluoromethylsulfonyl)-1H-imidazol-3-ium-1-yl, in which case the reaction may conveniently be effected at ambient temperature in an organic solvent such as acetonitrile.

In a variant procedure, the compounds of formula (I) above wherein Y represents —C(O)— may be prepared by a process which comprises reacting a compound of formula (VA), (VB), (VC), (VD) or (VE) as defined above with a compound of formula Z—$CO_2$H. Similarly, the compounds of formula (I) above wherein Y represents —C(O)C(O)— may be prepared by a process which comprises reacting a compound of formula (VA), (VB), (VC), (VD) or (VE) as defined above with a compound of formula Z—C(O)$CO_2$H.

The reaction is conveniently effected at ambient temperature in a suitable solvent, e.g. a dipolar aprotic solvent such as N,N-dimethylformamide, typically in the presence of a coupling reagent and a base. A suitable coupling reagent for use in the reaction may be O-(7-azabenzotriazol-1-yl)-N,N,N',N'-tetramethyluronium hexafluorophosphate (HATU). A suitable base for use in the reaction may be an organic base such as N,N-diisopropylethylamine.

In another procedure, the compounds of formula (I) above wherein Y represents —C(O)NH— may be prepared by a process which comprises reacting a compound of formula (VA), (VB), (VC), (VD) or (VE) as defined above with an isocyanate derivative of formula Z—N=C=O, wherein Z is as defined above.

The reaction is conveniently effected at a suitable temperature, e.g. ambient temperature or a temperature in the region of 0° C., in a suitable solvent or mixture of solvents. Such solvent or solvents may typically be selected as appropriate from an ethereal solvent such as 1,4-dioxane or tetrahydrofuran, a chlorinated solvent such as dichloromethane, a nitrile-containing solvent such as acetonitrile, and a dipolar aprotic solvent such as N,N-dimethylformamide. The reaction may optionally be performed in the presence of a base, e.g. an organic base such as diisopropylamine, N,N-diisopropylethylamine or triethylamine.

Alternatively, the compounds of formula (I) above wherein Y represents —C(O)NH— may be prepared by a process which comprises reacting a compound of formula (VA), (VB), (VC), (VD) or (VE) as defined above with a compound of formula Z—$NH_2$, wherein Z is as defined above, in the presence of triphosgene or 1,1'-carbonyldiimidazole.

The reaction is conveniently effected at ambient temperature in a suitable solvent, e.g. a chlorinated solvent such as dichloromethane, or a dipolar aprotic solvent such as N,N-dimethylformamide, typically in the presence of a base, e.g. an organic base such as N,N-diisopropylethylamine.

Alternatively, the compounds of formula (I) above wherein Y represents —C(O)NH— may be prepared by a two-step process which comprises: (i) reacting a compound of formula Z—$NH_2$, wherein Z is as defined above, with phenyl chloroformate; and (ii) reacting the material thereby obtained with a compound of formula (VA), (VB), (VC), (VD) or (VE) as defined above.

Step (i) of the above process is conveniently effected at a suitable temperature, e.g. ambient temperature or a temperature in the region of 0° C., in a suitable solvent, e.g. a cyclic ether solvent such as tetrahydrofuran or a chlorinated solvent such as dichloromethane, typically in the presence of a base, e.g. an organic base such as pyridine or triethylamine. Step (ii) is conveniently effected at ambient or elevated temperature in a suitable solvent, e.g. a sulfoxide solvent such as dimethyl sulfoxide, or a nitrile-containing solvent such as acetonitrile, or a $C_{1-4}$ alkanol such as ethanol, typically in the presence of a base, e.g. an organic base such as N,N-diisopropylethylamine.

In a further procedure, the compounds of formula (I) above wherein Y represents —$S(O)_2$NH— may be prepared by a two-step process which comprises: (i) reacting a compound of formula (VA), (VB), (VC), (VD) or (VE) as defined above with methyl trifluoromethanesulfonate; and (ii) reacting the material thereby obtained with a compound of formula Z—$NH_2$, wherein Z is as defined above.

Step (i) of the above process is conveniently effected at a temperature in the region of 0° C. in a suitable solvent, typically a chlorinated solvent such as dichloromethane. Step (ii) is conveniently effected at an elevated temperature in a suitable solvent, e.g. a nitrile-containing solvent such as acetonitrile.

In a further procedure, the compounds of formula (I) above wherein Y represents a covalent bond, and Z represents optionally substituted $C_{1-6}$ alkyl, optionally substituted $C_{3-7}$ cycloalkyl($C_{1-6}$)alkyl, optionally substituted $C_{3-7}$ heterocycloalkyl($C_{1-6}$)alkyl, optionally substituted aryl($C_{1-6}$)alkyl or optionally substituted heteroaryl($C_{1-6}$)alkyl, may be prepared by a process which comprises reacting a compound of formula (VA), (VB), (VC), (VD) or (VE) as defined above with a compound of formula $Z^1$-$L^3$ wherein $Z^1$ represents $C_{1-6}$ alkyl, $C_{3-7}$ cycloalkyl($C_{1-6}$)alkyl, aryl($C_{1-6}$)alkyl, $C_{3-7}$ heterocycloalkyl-($C_{1-6}$)alkyl or heteroaryl($C_{1-6}$)alkyl, any of which groups may be optionally substituted by one or more substituents, and $L^3$ represents a suitable leaving group.

The leaving group $L^3$ is typically a halogen atom.

The reaction is conveniently effected at ambient temperature in a suitable solvent, e.g. a dipolar aprotic solvent such as N,N-dimethylformamide, or a chlorinated solvent such as dichloromethane, typically in the presence of a base. A suitable base for use in the reaction may be an organic base such as triethylamine, or an inorganic base such as caesium carbonate.

In a variant procedure, the compounds of formula (I) above wherein Y represents a covalent bond, and Z represents optionally substituted $C_{1-6}$ alkyl, optionally substituted $C_{3-7}$ cycloalkyl($C_{1-6}$)alkyl, optionally substituted $C_{3-7}$ heterocycloalkyl($C_{1-6}$)alkyl, optionally substituted aryl($C_{1-6}$)

alkyl or optionally substituted heteroaryl($C_{1-6}$)alkyl, may be prepared by a two-step process which comprises: (i) reacting a compound of formula (VA), (VB), (VC), (VD) or (VE) as defined above with a compound of formula $Z^2$—CHO, wherein $Z^2$—$CH_2$— corresponds to a group of formula $Z^1$— as defined above; and (ii) reacting the material thereby obtained with a reducing agent.

Steps (i) and (ii) of the above process are conveniently effected at ambient temperature in a suitable solvent, e.g. a $C_{1-4}$ alkanol such as methanol. Step (i) is typically performed in the presence of a base, e.g. an organic base such as triethylamine. The reducing agent for use in step (ii) may suitably be an alkali metal borohydride such as sodium borohydride.

The compounds of formula (I) above wherein Y represents a linker group of formula (Ya) as defined above may be prepared by a process which comprises reacting a compound of formula (VA), (VB), (VC), (VD) or (VE) as defined above with a compound of formula (VI):

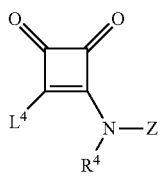
(VI)

wherein Z and $R^4$ are as defined above, and $L^4$ represents a suitable leaving group.

The leaving group $L^4$ is typically a $C_{1-4}$ alkoxy group, e.g. ethoxy.

The reaction is conveniently effected at ambient temperature in a suitable solvent, e.g. a lower alkanol such as ethanol, typically in the presence of a base, e.g. an organic base such as triethylamine.

The intermediates of formula (VA), (VB), (VC), (VD) or (VE) above may be prepared by reacting a compound of formula (III) as defined above with a compound of formula (VIIA), (VIIB), (VIIC), (VIID) or (VILE):

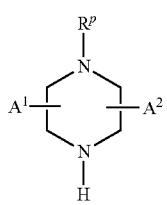
(VIIA)

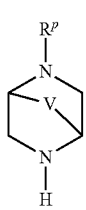
(VIIB)

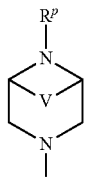
(VIIC)

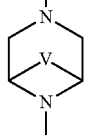
(VIID)

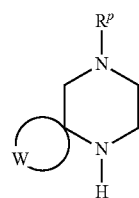
(VIIE)

wherein V, W, $A^1$ and $A^2$ are as defined above, and $R^p$ represents hydrogen or an N-protecting group; followed, as necessary, by removal of the N-protecting group $R^p$.

In one embodiment, the N-protecting group $R^p$ is typically tert-butoxycarbonyl (BOC).

In another embodiment, the N-protecting group $R^p$ is typically benzyl.

The reaction between compound (III) and compound (VIIA), (VIIB), (VIIC), (VIID) or (VIIE) is conveniently accomplished under conditions analogous to those described above for the reaction between compounds (III) and (IV).

Alternatively, the reaction between compound (III) and compound (VIIA), (VIIB), (VIIC), (VIID) or (VIIE) may be accomplished at a suitable temperature (ambient or elevated) in a solvent such as acetonitrile or N,N-dimethylformamide, ideally in the presence of a coupling agent such as benzotriazol-1-yloxytris(dimethylamino)-phosphonium hexafluorophosphate (BOP) or (benzotriazol-1-yloxy)tripyrrolidino-phosphonium hexafluorophosphate (PyBOP), and a base, e.g. an organic base such as 1,8-diazabicyclo[5.4.0]undec-7-ene (DBU).

In an alternative procedure, the intermediates of formula (VA), (VB), (VC), (VD) or (VE) above may be prepared by reacting a compound of formula $R^3$—$NHNH_2$ with a compound of formula (VIIIA), (VIIIB), (VIIIC), (VIIID) or (VIIIE):

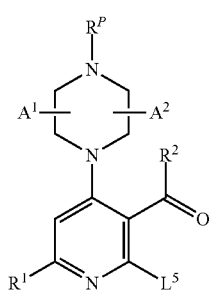
(VIIIA)

-continued

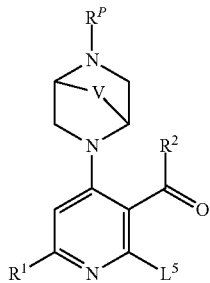
(VIIIB)

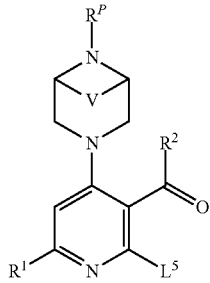
(VIIIC)

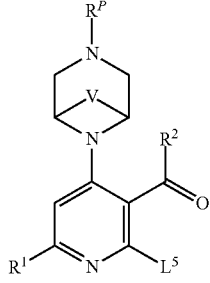
(VIIID)

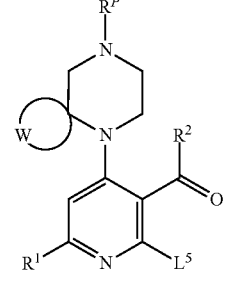
(VIIIE)

wherein V, W, $A^1$, $A^2$, $R^1$, $R^2$, $R^3$ and $R^p$ are as defined above, and $L^5$ represents a suitable leaving group; followed, as necessary, by removal of the N-protecting group $R^p$.

The leaving group $L^5$ is typically a halogen atom, e.g. chloro.

The reaction is conveniently effected at an elevated temperature in a suitable solvent, e.g. an ethereal solvent such as tetrahydrofuran, typically in the presence of a base, e.g. an organic base such as N,N-diisopropylethylamine.

Where the N-protecting group $R^p$ is BOC, subsequent removal of the BOC group may typically be accomplished by treatment with an acid, e.g. a mineral acid such as hydrochloric acid, or an organic acid such as trifluoroacetic acid. Alternatively, the BOC group may be removed by treatment with trimethylsilyl trifluoromethanesulfonate and 2,6-lutidine, typically at ambient temperature in a suitable solvent, e.g. a chlorinated solvent such as dichloromethane.

Where the N-protecting group $R^p$ is benzyl, subsequent removal of the benzyl group may typically be accomplished by catalytic hydrogenation. Suitably, transfer hydrogenation conditions will be employed. A suitable hydrogenation catalyst of use in this procedure may be a transition metal catalyst such as palladium on carbon. The reaction will conveniently be performed at ambient or elevated temperature in the presence of gaseous hydrogen or a hydrogen donor such as ammonium formate.

The intermediates of formula (VIIIA), (VIIIB), (VIIIC), (VIIID) or (VIIIE) above may be prepared by reacting a compound of formula (VIIA), (VIIB), (VIIC), (VIID) or (VIIE) as defined above with a compound of formula (IX):

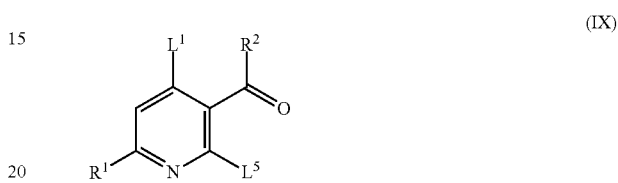
(IX)

wherein $R^1$, $R^2$, $L^1$ and $L^5$ are as defined above; under conditions analogous to those described above for the reaction between compound (III) and compound (VIIA), (VIIB), (VIIC), (VIID) or (VIIE).

The intermediates of formula (III) above wherein $R^1$ and $L^1$ are both chloro may be prepared by treating a compound of formula (X):

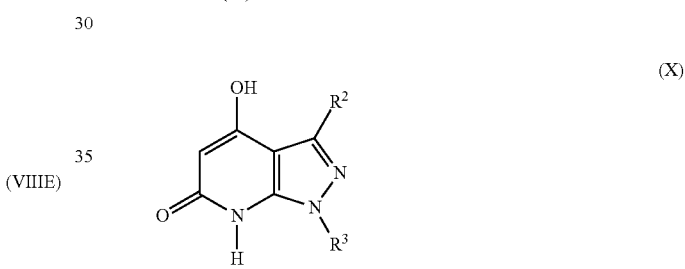
(X)

wherein $R^2$ and $R^3$ are as defined above; with a chlorinating agent.

A suitable chlorinating agent for use in the above procedure is phenylphosphonic dichloride.

The reaction is conveniently effected by mixing the reagents at an elevated temperature.

The intermediates of formula (X) above may be prepared by cyclisation of a compound of formula (XI):

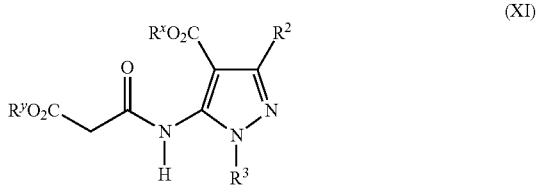
(XI)

wherein $R^2$ and $R^3$ are as defined above, and $R^x$ and $R^y$ independently represent $C_{1-4}$ alkyl;
followed by de-esterification and decarboxylation.

Suitably, $R^x$ represents methyl or ethyl, especially ethyl.

Suitably, $R^y$ represents methyl or ethyl, especially ethyl.

Cyclisation may be effected by treating compound (XI) with a strong base such as sodium hydride. Subsequent de-esterification and decarboxylation may be accomplished by treatment of the material thereby obtained with a base, typically an alkali metal hydroxide such as sodium hydroxide.

The intermediates of formula (XI) above wherein $R^y$ is ethyl may be prepared by reacting diethyl malonate with a compound of formula (XII):

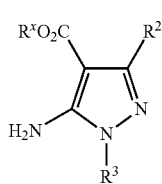

(XII)

wherein $R^2$, $R^3$ and $R^x$ are as defined above.

The reaction is conveniently effected by mixing the reagents at an elevated temperature.

As will be appreciated, the intermediates of formula (VA), (VB), (VC), (VD) and (VE) correspond to compounds in accordance with the present invention wherein Y represents a covalent bond and Z is hydrogen. Similarly, the intermediates of formula (VIIA), (VIIB), (VIIC), (VIID) or (VIIE) wherein $R^p$ is hydrogen correspond to intermediates of formula (IV) wherein Y represents a covalent bond and Z is hydrogen. Likewise, the intermediates of formula (VIIA), (VIIB), (VIIC), (VIID) or (VIIE) wherein $R^p$ is BOC correspond to intermediates of formula (IV) wherein Y represents —C(O)O— and Z is tert-butyl. Furthermore, the intermediates of formula (VIIA), (VIIB), (VIIC), (VIID) or (VIIE) wherein $R^p$ is benzyl correspond to intermediates of formula (IV) wherein Y represents a covalent bond and Z is benzyl.

Where they are not commercially available, the starting materials of formula (IV), (VI), (VIIA), (VIIB), (VIIC), (VIID), (VIIE), (IX) and (XII) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of example, a compound of formula (I) comprising a N-BOC moiety may be converted into the corresponding compound comprising a N—H moiety by treatment with an acid, e.g. a mineral acid such as hydrochloric acid, or an organic acid such as trifluoroacetic acid.

A compound of formula (I) wherein $R^1$ represents halogen, e.g. chloro, may be converted into the corresponding compound wherein $R^1$ represents amino (—NH$_2$) in a two-step procedure which comprises: (i) treatment with benzylamine; and (ii) removal of the benzyl moiety from the material thereby obtained by catalytic hydrogenation.

A compound of formula (I) wherein $R^1$ represents —SR$^a$ may be converted into the corresponding compound wherein $R^1$ represents —SO$_2$R$^a$ by treatment with an oxidising agent, typically 3-chloroperoxybenzoic acid (MCPBA).

A compound of formula (I) wherein $R^1$ represents —SO$_2$R$^a$, e.g. methylsulfonyl, may be converted into the corresponding compound wherein $R^1$ represents —OR$^a$ by treatment with a sodium salt of formula NaOR$^a$. Similarly, a compound of formula (I) wherein $R^1$ represents —SO$_2$R$^a$, e.g. methylsulfonyl, may be converted into the corresponding compound wherein $R^1$ represents cyano by treatment with a cyanide salt, e.g. an alkali metal cyanide salt such as sodium cyanide. Likewise, a compound of formula (I) wherein $R^1$ represents —SO$_2$R$^a$, e.g. methylsulfonyl, may be converted into the corresponding compound wherein $R^1$ represents —NR$^b$R$^c$ by treatment with an amine of formula H—NR$^b$R$^c$.

A compound of formula (I) wherein $R^2$ represents —CO$_2$R$^d$, in which $R^d$ is other than hydrogen, may be converted into the corresponding compound wherein $R^2$ represents carboxy (—CO$_2$H) by treatment with a base, typically an alkali metal hydroxide such as sodium hydroxide. A compound of formula (I) wherein $R^2$ represents carboxy (—CO$_2$H) may be converted into the corresponding compound wherein $R^2$ represents —CONR$^b$R$^c$ or —CON(OR$^a$)R$^b$ by treatment with the appropriate reagent of formula H—NR$^b$R$^c$ or H—N(OR$^a$)R$^b$ respectively, typically in the presence of a coupling agent such as 1-(3-dimethylaminopropyl)-3-ethylcarbodiimide hydrochloride (EDC) and an additive such as 1-hydroxybenzotriazole hydrate (HOBT), optionally in the presence of a base, e.g. an organic base such as N,N-diisopropylethylamine.

A compound of formula (I) wherein $R^2$ represents carboxy (—CO$_2$H) may be converted into the corresponding compound wherein $R^2$ represents —CONH$_2$ by treatment with ammonium chloride, typically in the presence of a coupling agent such as EDC and an additive such as HOBT, suitably in the presence of a base, e.g. an organic base such as diisopropylamine or N,N-diisopropylethylamine. A compound of formula (I) wherein $R^2$ represents —CONH$_2$ may be converted into the corresponding compound wherein $R^2$ represents cyano (—CN) by treatment with phosphorus oxychloride. Alternatively, a compound of formula (I) wherein $R^2$ represents —CONH$_2$ may be converted into the corresponding compound wherein $R^2$ represents cyano in a two-step procedure which comprises: (i) treatment with cyanuric chloride; and (ii) treatment of the material thereby obtained with water.

A compound of formula (I) wherein $R^2$ represents carboxy (—CO$_2$H) may be converted into the corresponding compound wherein $R^2$ represents hydroxymethyl (—CH$_2$OH) in a two-step procedure which comprises: (i) treatment with ethyl chloroformate and triethylamine; and (ii) treatment of the material thereby obtained with a reducing agent, typically an alkali metal borohydride such as sodium borohydride.

A compound of formula (I) wherein $R^2$ represents carboxy (—CO$_2$H) may be converted into the corresponding compound wherein $R^2$ represents hydroxy in a two-step procedure which comprises: (i) treatment with diphenyl phosphoryl azide; and (ii) treatment of the material thereby obtained with water.

A compound of formula (I) wherein $R^2$ represents carboxy (—CO$_2$H) may be converted into the corresponding compound wherein $R^2$ represents —NHCO$_2$R$^d$, wherein $R^d$ is other than hydrogen, in a two-step procedure which comprises: (i) treatment with diphenyl phosphoryl azide; and (ii) treatment of the material thereby obtained with the appropriate reagent of formula R$^d$—OH.

A compound of formula (I) wherein $R^2$ represents carboxy (—CO$_2$H) may be converted into the corresponding compound wherein $R^2$ represents a 3-substituted 1,2,4-oxadiazol-5-yl moiety in a two-step procedure which comprises: (i) treatment with an appropriately-substituted N'-hydroxyamidine derivative, typically in the presence of a coupling agent such as O-(7-azabenzotriazol-1-yl)-N,N,N',N'-tetramethyluronium hexafluorophosphate (HATU), suitably in the presence of a base, e.g. an organic base such as N,N-diisopropylethylamine; and (ii) treatment of the material thereby obtained with a strong base, suitably a strong inorganic base, e.g. an alkali metal tert-butoxide such as potassium tert-butoxide.

A compound of formula (I) wherein $R^3$ represents hydrogen may be converted into the corresponding compound wherein $R^3$ represents $C_{1-6}$ alkyl, e.g. methyl, by treatment with a $C_{1-6}$ alkyl halide, e.g. iodomethane, usually in the presence of a base, suitably a strong inorganic base, e.g. sodium hydride.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T.W. Greene & P.G.M. Wuts, *Protective Groups in Organic Synthesis*, John Wiley & Sons, $3^{rd}$ edition, 1999. The protecting groups may be removed at any convenient subsequent stage utilising methods known from the art.

The following Examples illustrate the preparation of compounds according to the invention.

The compounds in accordance with this invention potently inhibit the activity of human PI4KIIIβ.

PI4KIIIβ Enzyme Inhibition Assay

Procedure A

Compounds were assayed utilizing reagents from Invitrogen and Promega. Compounds were screened in 1% DMSO (final) as 3-fold serial dilutions from a starting concentration of 20 μM. The 2.5× PI4Kβ reagent, the 2.5× PI Lipid Kinase Substrate/ATP mixture and the 5× compounds were prepared in 20 mM Tris pH 7.5, 0.5 mM EGTA, 2 mM DTT, 5 mM $MgCl_2$, 0.4% Triton. The final 25 μL Kinase Reaction consisted of: 4 nM PI4Kβ, 100 μM PI Lipid Kinase Substrate (both Invitrogen), and compound. The final ATP concentration in the assay was 10 μM. The detection reagents consisted of ADP-Glo™ Reagent and ADP-Glo™ Detect Reagent (Promega).

Briefly, compound was added to PI4Kβ followed by addition of ATP/PI Lipid Kinase Substrate mixture. The reaction mixture was incubated for 60 minutes at room temperature. The ADP-Glo™ Reagent was added and the plate was incubated for 40 minutes at room temperature, followed by addition of ADP-Glo™ Detect Reagent. The plate was incubated for a further 120 minutes and read on a Luminescence plate reader. The data was fitted with XL fit from IDBS using model number 205.

Procedure B

Compounds were assayed using a PI4Kbeta Adapta assay. Compounds were screened in 1% DMSO (final) as 3-fold serial dilutions from a starting concentration of 10 μM. The 2× PI4 KB (PI4K beta)/PI Lipid Kinase Substrate mixture was prepared in 50 mM HEPES pH 7.5, 0.1% CHAPS, 1 mM EGTA, 4 mM $MgCl_2$. The final 10 μL Kinase Reaction consisted of 7.5-60 ng PI4Kβ, and 100 μM PI Lipid Kinase Substrate in 32.5 mM HEPES pH 7.5, 0.05% CHAPS, 0.5 mM EGTA, 2 mM $MgCl_2$. The final ATP concentration in the assay was 10 μM. The detection mix consisted of EDTA (30 mM), Eu-anti-ADP antibody (6 nM) and ADP tracer. The detection mix contained the EC60 concentration of tracer for 5-150 μM ATP.

Briefly, ATP was added to compound, followed by addition of a PI4Kβ/PI Lipid Kinase Substrate mixture. The plate was shaken for 30 seconds to mix, then briefly centrifuged. The reaction mixture was incubated for 60 minutes at room temperature. The detection mix was added, then the plate was shaken and centrifuged. The plate was incubated for 60 minutes at room temperature and read on a fluorescence plate reader. The data was fitted with XL fit from IDBS using model number 205.

When tested in the above assay (Procedure A or Procedure B), the compounds of the accompanying Examples were all found to possess $IC_{50}$ values for inhibition of the activity of human PI4KIIIβ of 50 μM or better.

Certain compounds in accordance with this invention are potent inhibitors when measured in the MLR test described below.

The Mixed Lymphocyte Reaction (MLR) Test

Human peripheral blood mononuclear cells (PBMCs) were isolated from buffy coats, obtained from healthy blood donors by Ficoll (Lymphoprep, Axis-Shield PoC AS, Oslo, Norway) density-gradient centrifugation. The cells at the Ficoll-plasma interface were washed three times and used as "Responder" cells. RPMI 1788 (ATCC, No. CCL-156) cells were treated with mitomycin C (Kyowa, Nycomed, Brussels, Belgium) and used as "Stimulator" cells. Responder cells (0.12×106), Stimulator cells (0.045×106) and compounds (in different concentrations) were cocultured for 6 days in RPMI 1640 medium (BioWhittaker, Lonza, Belgium) supplemented with 10% fetal calf serum, 100 U/ml Geneticin (Gibco, LifeTechnologies, UK). Cells were cultured in triplicate in flat-bottomed 96-well microtiter tissue culture plates (TTP, Switzerland). After 5 days, cells were pulsed with 1 μCi of methyl-$^3$H thymidine (MP Biomedicals, USA), harvested 18 h later on glass filter paper and counted. Proliferation values were expressed as counts per minute (cpm), and converted to % inhibition with respect to a blank MLR test (identical but without added compound). The $IC_{50}$ was determined from a graph with at least four points, each derived from the mean of 2 experiments. The IC$_{50}$ value represents the lowest concentration of test compound (expressed in μM) that resulted in a 50% inhibition of the MLR.

Certain compounds of the accompanying Examples were found to generate IC$_{50}$ values in the MLR test of 10 μM or better.

EXAMPLES

| Abbreviations | |
| --- | --- |
| THF: | tetrahydrofuran |
| DMA: | N,N-dimethylacetamide |
| DCM: | dichloromethane |
| EtOH: | ethanol |
| AcOH: | acetic acid |
| Et$_3$N: | triethylamine |
| h: | hour |
| MS: | Mass Spectrometry |
| RT: | retention time |
| LCMS: | Liquid Chromatography Mass Spectrometry |
| HPLC: | High Performance Liquid Chromatography |
| MeOH: | methanol |
| DMF: | N,N-dimethylformamide |
| DIPEA: | N,N-diisopropylethylamine |
| EtOAc: | ethyl acetate |
| DMSO: | dimethyl sulfoxide |
| IMS: | industrial methylated spirits |
| r.t.: | room temperature |
| M: | mass |

Analytical Methods
Method 1
High pH (approximately pH 9.5)
Column: Waters XBridge, C18, 2.1×20 mm, 2.5 μm
Solvent A: 10 mM ammonium formate in water+0.1% ammonia solution
Solvent B: acetonitrile+5% solvent A+0.1% ammonia solution
Gradient Program:

| Time | A % | B % |
| --- | --- | --- |
| 0.00 | 95.0 | 5.0 |
| 1.50 | 5.0 | 95.0 |
| 2.50 | 5.0 | 95.0 |
| 3.00 | 95.0 | 5.0 |

Method 2
High pH (approximately pH 9.5)
Column: Waters XBridge, C18, 2.1×20 mm, 2.5 μm
Solvent A: 10 mM ammonium formate in water+0.1% ammonia solution
Solvent B: acetonitrile+5% solvent A+0.1% ammonia solution
Gradient Program:

| Time | A % | B % |
| --- | --- | --- |
| 0.00 | 95.0 | 5.0 |
| 4.00 | 5.0 | 95.0 |
| 5.00 | 5.0 | 95.0 |
| 5.10 | 95.0 | 5.0 |

Intermediate 1

Ethyl 5-[(3-ethoxy-3-oxopropanoyl)amino]-1-methylpyrazole-4-carboxylate

A solution of ethyl 5-amino-1-methylpyrazole-4-carboxylate (5 g, 29.6 mmol) in diethyl malonate (9 mL, 59.2 mmol) was heated at 180° C. overnight, then for a further 6 h at 200° C. After this time, the reaction mixture was cooled and concentrated in vacuo, then purified by normal phase chromatography (SiO$_2$, 50% EtOAc/heptane to 100% EtOAc), to yield the title compound (4.12 g, 49%) as a pale yellow oil that crystallised on standing. δ$_H$ (CDCl$_3$) 9.70 (br s, 1H), 7.79 (s, 1H), 4.27 (2×q, J 6.8 Hz, 4H), 3.75 (s, 3H), 3.50 (s, 2H), 1.32 (2×t, J 7.4 Hz, 6H).

Intermediate 2

4-Hydroxy-1-methyl-7H-pyrazolo[3,4-b]pyridin-6-one

To a solution of Intermediate 1 (4.12 g, 14.56 mmol) in DMA (50 mL) at 0° C. (ice bath) was added NaH (60% suspension in mineral oil, 1.3 g, 32.02 mmol). The reaction mixture was slowly warmed to room temperature, then heated at 100° C. After 30 minutes, the reaction mixture was cooled and poured onto diethyl ether, then the yellow solid was collected by filtration. The solid was dissolved in water (20 mL) and 2N aqueous NaOH solution (7.3 mL) was added. The mixture was heated at reflux for 18 h. A further aliquot of solid NaOH (2 equivalents) was added, and the mixture was heated for a further 6 h. After this time, another aliquot of solid NaOH (2 equivalents) was added, and the reaction mixture was heated for another 18 h. The reaction mixture was cooled to room temperature, then diluted with water (10 mL) and acidified to pH 5 with concentrated HCl. The precipitate formed was filtered under vacuum and oven-dried overnight, to yield the title compound (2.08 g, 87%) as a white solid. δ$_H$ (DMSO-d$_6$) 11.40 (br s, 1H), 7.67 (s, 1H), 5.42 (br s, 1H), 3.75 (s, 3H).

Intermediate 3

4,6-Dichloro-1-methylpyrazolo[3,4-b]pyridine

Phenylphosphonic dichloride (1.03 mL, 7.32 mmol) was added to solid Intermediate 2 (0.2 g, 1.22 mmol) and the mixture was heated at 170° C. overnight. The reaction mixture was cooled and poured onto ice with stirring, then the mixture was basified with aqueous ammonia. The precipitate was collected by filtration under vacuum, and dried overnight in a vacuum oven, to yield the title compound (0.17 g, 69%) as a grey solid. δ$_H$ (CDCl$_3$) 8.04 (s, 1H), 7.16 (s, 1H), 4.11 (s, 3H).

Intermediate 4

4-[(2S)-4-Benzyl-2-methylpiperazin-1-yl]-6-chloro-1-methylpyrazolo[3,4-b]pyridine To a solution of (3S)-1-benzyl-3-methylpiperazine hydrochloride (0.53 g, 2.29 mmol) in n-butanol (2.6 mL) were added DIPEA (1.6 mL, 9.35 mmol) and Intermediate 3 (0.47 g, 2.34 mmol). The reaction mixture was heated at 140° C. for 21 h, then for a further 3 days at 150° C. After this time, the reaction mixture was cooled and concentrated in vacuo. The residue was purified by column chromatography (silica gel 100-200 mesh, 9:1 EtOAc/heptane then 5:1 EtOAc/heptane) to yield the title compound (0.08 g, 10%) as a brown oil. δ$_H$(CDCl$_3$) 7.88 (s, 1H), 7.30-7.60 (m, 5H), 6.24 (s, 1H), 4.25-4.40 (m, 1H), 4.01 (s, 3H), 3.72-3.80 (m, 1H), 3.50-3.60 (m, 3H), 2.92-3.00 (m, 1H), 2.76-2.79 (m, 1H), 2.38 (d, J 3.7 Hz, 1H), 2.25 (app. t, J 3.6, 1H), 1.35 (d, J 6.5 Hz, 3H).

Intermediate 5

N-Benzyl-4-[(2S)-4-benzyl-2-methylpiperazin-1-yl]-1-methylpyrazolo[3,4-b]pyridin-6-amine Intermediate 4 (0.12 g, 0.33 mmol), benzylamine (1.5 mL) and 1-butyl-3-methyl-imidazolium hexafluorophosphate additive (2 drops) were placed in a microwave tube and heated at 170° C. for 4 h using a Biotage Initiator 60 (300 W). The mixture was next heated at 185° C. for 2 h, then at 195° C. for 2.5 h. EtOAc was added, then the mixture was washed with water (×2) and extracted with EtOAc. The organic layers were dried over Na$_2$SO$_4$ and concentrated in vacuo. The residue was purified by column chromatography (silica gel 100-200 mesh, EtOAc) to yield the title compound (0.1 g, 70%) as a pale green gum. LCMS (ES+) [M+H]$^+$ 427, RT 2.29 minutes (method 1).

Intermediate 6

4-[(2S)-2-Methylpiperazin-1-yl]-1-methylpyrazolo[3,4-b]pyridin-6-amine

To a solution of Intermediate 5 (0.1 g, 0.24 mmol) in IMS (5 mL) were added 5% Pd/C (0.02 g) and ammonium formate (10 equivalents, 0.15 g). The reaction mixture was heated at 85° C. overnight, then cooled, filtered through Celite, flushed with methanol and concentrated in vacuo. The resultant gum was triturated with diethyl ether to give the title compound (0.034 g, 58%) as a white solid. LCMS (ES+) [M+H]$^+$ 247.12, RT 1.04 minutes (method 1).

Intermediate 7

1-Methyl-4-[(2S)-2-methylpiperazin-1-yl]pyrazolo[3,4-b]pyridine hydrochloride

Intermediate 4 (0.6 g, 1.67 mmol) was dissolved in EtOH (5 mL) and 10% Pd/C (0.018 g) was added. The reaction mixture was stirred under a hydrogen atmosphere overnight. The catalyst was removed by filtration through a pad of Celite and the mixture was concentrated in vacuo. The resulting foam was triturated with DCM, to yield the title compound (0.280 g, 71.8%) as a white solid. δ$_H$(400 MHz, DMSO-d$_6$) 9.34 (s, 2H), 8.26 (s, 1H), 8.20-8.15 (m, 1H), 6.49 (d, 1H, J 5.7 Hz), 5.76 (s, 1H), 4.73-4.64 (m, 1H), 4.06-3.90 (m, 4H), 3.55-3.45 (m, 1H), 3.39-3.26 (m, 1H), 3.19-3.07 (m, 1H), 1.30 (d, 3H, J 7.0 Hz).

Intermediate 8

4-[(2S)-4-Benzyl-2-ethylpiperazin-1-yl]-6-chloro-1-methylpyrazolo[3,4-b]pyridine (3S)-1-Benzyl-3-ethylpiperazine (9.8 mmol, 2.0 g) and Intermediate 3 in 1-butanol (20 mL) with DIPEA (29 mmol, 5 mL) was heated at 190° C. for 15 days. The reaction mixture was concentrated in vacuo and purified on silica, with an EtOAc in isohexane gradient, to give the title compound (1.5 g, 41%) as an oil. LCMS (ES+) 370 [M+H]$^+$, RT 2.59 minutes (method 1).

Intermediate 9

N-Benzyl-4-[(2S)-4-benzyl-2-ethylpiperazin-1-yl]-1-methylpyrazolo[3,4-b]pyridin-6-amine Intermediate 8 (1.5 g, 4.06 mmol) was suspended in benzylamine (2 mL) and the reaction mixture was heated at 200° C. for 24 h in a Biotage Initiator Plus microwave oven. The reaction mixture was allowed to cool, then diluted with EtOAc. The organic layer was washed with water, dried over Na$_2$SO$_4$ and filtered. Upon concentration in vacuo the highly mobile oil was purified by column chromatography, using a 20-100% EtOAc in hexane gradient, to give the title compound (1.8 g, 100%). LCMS (ES+) 441 [M+H]$^+$, RT 1.68 minutes (method 1).

Intermediate 10

4-[(2S)-2-Ethylpiperazin-1-yl]-1-methylpyrazolo[3,4-b]pyridin-6-amine

Intermediate 9 (1.2 g, 2.7 mmol) was dissolved in EtOH (5 mL) and 10% Pd/C (0.03 g) was added. The reaction mixture was stirred under a hydrogen atmosphere overnight. The catalyst was removed by filtration through a pad of Celite and the resulting solution was concentrated in vacuo. The residue was re-dissolved in acetic acid and stirred at 50° C. under a hydrogen atmosphere overnight. Upon cooling, the catalyst was removed by filtration through a pad of Celite. The resulting mixture was concentrated in vacuo to give the title compound (0.71 g, 100%) as a yellow oil. LCMS (ES+) 261 [M+H]$^+$, RT 0.9 minutes (method 1).

Intermediate 11 tert-Butyl (3S)-4-(2-chloro-3-formylpyridin-4-yl)-3-ethylpiperazine-1-carboxylate tert-Butyl (3R)-3-ethylpiperazine-1-carboxylate (1.1 g, 5.1 mmol) was suspended in 1-butanol (8.1 g, 110 mmol) and DIPEA (1.3 g, 10 mmol) and 2,4-dichloropyridine-3-carbaldehyde (0.90 g, 5.1 mmol) was added. The suspension was heated at 70° C. for 5 h. The reaction mixture was concentrated in vacuo and the residue was purified by column chromatography, using an EtOAc/hexane gradient, to give the title compound (0.45 g, 25%) as a yellow oil. LCMS (ES+) 354 [M+H]$^+$, RT 1.47 minutes (method 1).

Intermediate 12 tert-Butyl (3S)-3-ethyl-4-(1-methylpyrazolo[3,4-b]pyridin-4-yl)piperazine-1-carboxylate Intermediate 11 (0.4 g, 1.13 mmol) was dissolved in THF (8.8 g) and DIPEA (0.29 g, 2.26 mmol) was added, followed by methyl hydrazine (0.062 g, 1.36 mmol). The reaction mixture was heated at 70° C. overnight, then concentrated in vacuo. The residue was dissolved in AcOH and heated at 50° C. for 4 h. Upon cooling, the reaction mixture was concentrated in vacuo and the residue was suspended between DCM and 2M aqueous NaOH solution. The aqueous layer was further extracted with DCM, and the combined organic layers were dried over Na$_2$SO$_4$, then filtered and concentrated in vacuo. The resulting brown oil was purified by column chromatography, using an EtOAc/hexane gradient, to give the title compound (0.2 g, 51.2%). LCMS (ES+) 346 [M+H]$^+$, RT 1.42 minutes (method 1).

Intermediate 13

4-[(2S)-2-Ethylpiperazin-1-yl]-1-methylpyrazolo[3,4-b]pyridine dihydro chloride

Intermediate 12 (0.2 g, 0.58 mmol) was dissolved in EtOH (4 mL) and 4M HCl in 1,4-dioxane (20 mmol) was added. The reaction mixture was left to stand for 1 h, then concentrated in vacuo, to yield the title compound (0.18 g, 100.0%) as a colourless glass. LCMS (ES+) 246 [M+H]$^+$, RT 1.06 minutes (method 1).

Intermediate 14 tert-Butyl (3S)-4-(2-chloro-3-formylpyridin-4-yl)-3-(2-hydroxyethyl)piperazine-1-carboxylate tert-Butyl (3S)-3-(2-hydroxyethyl)piperazine-1-carboxylate (0.48 g, 2.08 mmol) was suspended in 1-butanol (8.1 g) and DIPEA (0.54 g, 4.17 mmol). 2,4-Dichloropyridine-3-carbaldehyde (0.37 g, 2.08 mmol) was added and the suspension was heated at 70° C. for 5 h. The reaction mixture was concentrated in vacuo and the residue was purified by column chromatography, using an EtOAc/hexane gradient, to give the title compound (0.2 g, 25.9%) as a yellow oil. LCMS (ES+) 370 [M+H]$^+$, RT 1.31 minutes (method 1).

Intermediate 15 tert-Butyl (3S)-3-(2-hydroxyethyl)-4-(1-methylpyrazolo[3,4-b]pyridin-4-yl)piperazine-1-carboxylate Intermediate 14 (0.2 g, 0.54 mmol) was dissolved in THF (8.8 g) and DIPEA (0.14 g, 1.08 mmol) was added, followed by methylhydrazine (0.03 g, 0.65 mmol). The reaction mixture was heated at 70° C. overnight, then concentrated in vacuo. The residue was dissolved in AcOH and heated at 50° C. for 4 h. Upon cooling, the reaction mixture was concentrated in vacuo and the residue was suspended between DCM and 2M aqueous NaOH solution. The aqueous layer was further extracted with DCM, then the combined organic layers were dried over sodium sulfate, filtered and concentrated in vacuo. The resulting brown oil was purified by column chromatography, using an EtOAc/hexane gradient, to give the title compound (0.16 g, 79.3%). LCMS (ES+) 362 [M+H]$^+$, RT 1.27 minutes (method 1).

Intermediate 16

2-[(2S)-1-(1-Methylpyrazolo[3,4-b]pyridin-4-yl)piperazin-2-yl]ethanol dihydrochloride Intermediate 15 (0.16 g, 0.43 mmol) was dissolved in EtOH (5 mL) and 4M HCl in 1,4-dioxane (20 mmol) was added. The reaction mixture was left to stand for 1 h, then concentrated in vacuo, to yield the title compound (0.14 g, 99.98%). LCMS (ES+) 262 [M+H]$^+$, RT 0.91 minutes (method 1).

Intermediate 17

6-Methyl-5-nitro-2-(prop-2-yloxy)pyridine

To a solution of 6-methyl-5-nitropyridin-2-ol (1.5 g, 9.7 mmol) in DMF (8 mL) was added Cs$_2$CO$_3$ (6.2 g, 19 mmol) and the reaction mixture was stirred at room temperature for 15 minutes. Isopropyl methanesulfonate (2.68 g, 19 mmol) was added and the reaction mixture was heated at 80° C. for 2 h, then diluted with EtOAc (100 mL). The organic layer was washed with water, then separated, dried over Na$_2$SO$_4$ and concentrated in vacuo. The residue was purified by silica gel (100:200 mesh) column chromatography, using 5% EtOAc in hexane as eluent, to afford the title compound (1.2 g, 63%). δ$_H$ (DMSO-d$_6$) 8.33 (d, J 8.98 Hz, 1H), 6.79 (d, J 8.98 Hz, 1H), 5.37 (m, 1H), 2.70 (s, 3H), 1.11-1.38 (m, 6H).

Intermediate 18

2-Methyl-6-(prop-2-yloxy)pyridin-3-amine

To a stirred solution of Intermediate 17 (1.2 g, 6.1 mmol) in MeOH (20 mL) at 0° C. were added zinc (1.99 g, 30 mmol) and ammonium formate (1.89 g, 30 mmol) portionwise. The reaction mixture was stirred at room temperature for 1 h, then filtered through celite. The filtrate was concentrated in vacuo. The residue was diluted with water, then extracted with DCM. The organic layer was separated, dried over Na$_2$SO$_4$, and concentrated in vacuo. The residue was purified by silica gel (100:200 mesh) column chromatography, using 20% EtOAc in hexane as eluent, to afford a solid that was further washed with pentane to yield the title compound (0.7 g, 70%). δ$_H$ (DMSO-d$_6$) 6.94 (d, J 8.53 Hz, 1H), 6.32 (d, J 8.53 Hz, 1H), 5.04 (m, 1H), 4.44 (s, 2H), 2.18 (s, 3H), 1.20 (d, J 6.28 Hz, 6H).

Intermediate 19

Phenyl N-[2-methyl-6-(prop-2-yloxy)pyridin-3-yl]carbamate

To a solution of Intermediate 18 (0.1 g, 0.6 mmol) in THF (5 mL) at 0° C. was added pyridine (0.06 g, 0.75 mmol), and the reaction mixture was stirred at room temperature for 10 minutes. Phenyl chloroformate (0.1 g, 0.63 mmol) was added and the reaction mixture was stirred at room temperature for 2 h. The reaction mixture was diluted with water and extracted with EtOAc. The organic layer was separated and dried over Na$_2$SO$_4$, then concentrated in vacuo, to afford the title compound (0.24 g, 70%). δ$_H$ (DMSO-d$_6$) 9.51 (s, 1H), 7.71-7.09 (m, 5H), 6.66 (m, 2H), 5.35-5.12 (m, 1H), 2.37 (d, J 3.4 Hz, 3H), 1.37-1.12 (m, 6H).

Intermediate 20

Phenyl N-(6-methoxy-2-methylpyridin-3-yl)carbamate

To a solution of 6-methoxy-2-methylpyridin-3-amine (2.02 g, 13.9 mmol) in DCM (50 mL) were added triethylamine (2.3 mL, 17 mmol) and phenyl chloroformate (1.9 mL, 15 mmol). The mixture was stirred under nitrogen at r.t. overnight, then washed with saturated aqueous sodium bicarbonate solution. The organic layer was separated and concentrated in vacuo. To the resulting brown oil was added diethyl ether. Following the addition of isohexane, a solid precipitated out of solution, to yield the title compound (2.79 g, 56.0%) as an off-white/pale pink solid. LCMS (ES+) 259.8 [M+H]$^+$, RT 1.77 minutes (method 1).

Intermediates 21 to 36

To a cooled (ice bath) solution of the appropriate amine (1 mmol) in THF (50 mL) was added pyridine (1.1 equivalents), followed by phenyl chloroformate (1 equivalent) dropwise. The reaction mixture was allowed to warm to room temperature. When LCMS confirmed complete conversion of the amine to the desired carbamate, the reaction mixture was quenched with water. The title compound was then either collected by filtration, or extracted into DCM, phase separated and concentrated in vacuo, and used without further purification.

| Int. | Name | LCMS Data | | |
|---|---|---|---|---|
| | | RT | [M + H]$^+$ | Method |
| 21 | Phenyl N-[2-methyl-4-(trifluoromethoxy)phenyl]-carbamate | 2.26 | 312.2 | 1 |
| 22 | Phenyl N-[6-(difluoromethoxy)-2-methylpyridin-3-yl]carbamate | 0.98 | 295.2 | 1 |
| 23 | Phenyl N-(6-ethoxy-2-methylpyridin-3-yl)carbamate | 1.45 | 273 | 1 |
| 24 | Phenyl N-(imidazo[1,2-a]pyridin-8-yl)carbamate | — | 254.1 | 1 |
| 25 | Phenyl N-[4-(difluoromethoxy)-2-methylphenyl]-carbamate | 1.45 | 294 | 1 |
| 26 | Phenyl N-(6-methoxy-5-methylpyridin-3-yl)-carbamate | 1.38 | 259 | 1 |
| 27 | Phenyl N-[6-(3,3-difluoroazetidin-1-yl)-2-methyl-pyridin-3-yl]carbamate | 1.34 | 320.2 | 1 |
| 28 | Phenyl N-(2,6-dimethoxypyridin-3-yl)carbamate | 1.44 | 275 | 1 |
| 29 | Phenyl N-[5-methoxy-6-(trifluoromethyl)pyridin-2-yl]carbamate | 2.14 | 313 | 2 |
| 30 | Phenyl N-(4-isopropoxy-2-methylphenyl)carbamate | 2.20 | 286 | 2 |
| 31 | Phenyl N-(4-methoxy-2-methylphenyl)carbamate | 1.87 | 258 | 2 |
| 32 | Phenyl N-(4-methoxy-3-methylphenyl)carbamate | 2.02 | 258 | 2 |
| 33 | Phenyl N-[6-(dimethylamino)-2-methylpyridin-3-yl]-carbamate | 1.79 | 272 | 2 |
| 34 | Phenyl N-[5-(dimethylamino)-3-methylpyrazin-2-yl]-carbamate | 2.07 | 273 | 2 |
| 35 | Phenyl N-(6-bromo-5-methoxy-pyridin-2-yl)-carbamate | 2.72 | 325 | 2 |
| 36 | Phenyl N-(6-chloro-5-methoxy-pyridin-2-yl)-carbamate | 2.78 | 279 | 2 |

Intermediate 37

3-Methoxy-6-nitropicolinonitrile

To a stirred solution of 2-bromo-3-methoxy-6-nitropyridine (1.5 g, 6.46 mmol) in DMF (20 mL) was added zinc cyanide (1.16 g, 12.9 mmol) at r.t. The reaction mixture was heated at 120° C. for 4 h, then quenched with H$_2$O (50 mL). The aqueous layer was extracted with EtOAc (2×50 mL), then the organic layer was washed with H$_2$O (25 mL) and brine (25 mL). The organic layer was separated, dried over anhydrous Na$_2$SO$_4$ and concentrated in vacuo. The solid obtained was triturated in pentane to afford the title compound (0.9 g, 78%) as a solid. δ$_H$ (400 MHz, DMSO-d$_6$) 8.65 (d, J 9.3 Hz, 1H), 8.10 (d, J 9.2 Hz, 1H), 4.13 (s, 3H).

Intermediate 38

6-Amino-3-methoxypicolinonitrile

To a stirred solution of Intermediate 37 (0.9 g, 5.02 mmol) in EtOH (10 mL) were added iron powder (0.56 g, 10.04 mmol) and AcOH (0.2 mL) at room temperature. The reaction mixture was heated at 90° C. for 3 h, then filtered through Celite. The filtrate was concentrated in vacuo. The crude residue was dissolved in EtOAc (25 mL), then the organic layer was washed with H$_2$O (10 mL) and brine (10 mL). The organic layer was dried over Na$_2$SO$_4$ and concentrated in vacuo to afford the title compound (600 mg, 80%) as a semi-solid. δ$_H$ (400 MHz, DMSO-d$_6$) 7.51 (d, J 9.3 Hz, 1H), 6.78 (d, J 9.3 Hz, 1H), 6.08 (s, 2H), 3.80 (s, 3H). LCMS (ES+) [M+H]$^+$ 150, RT 1.75 minutes (method 2).

Intermediate 39

Phenyl N-(6-cyano-5-methoxypyridin-2-yl)carbamate

To a stirred solution of Intermediate 38 (0.6 g, 4.02 mmol) in THF (10 mL), maintained at 0° C., was added pyridine (0.48 mL, 6.04 mmol), followed by phenyl chloroformate (0.75 g, 4.83 mmol). The reaction mixture was stirred at room temperature for 1 h, then diluted with H$_2$O (20 mL) and extracted with EtOAc (2×25 mL). The organic layer was separated, dried over anhydrous Na$_2$SO$_4$ and concentrated under reduced pressure to afford the title compound (0.6 g, 54%). δ$_H$ (400 MHz, DMSO-d$_6$) 10.94 (s, 1H), 8.08 (d, J 9.3 Hz, 1H), 7.87 (d, J 9.4 Hz, 1H), 7.42 (t, J 7.7 Hz, 2H), 7.24 (dd, J 25.7, 7.7 Hz, 3H), 3.94 (s, 3H). LCMS (ES+) [M+H]$^+$ 270.0, RT 2.38 minutes (method 2).

Example 1

(3S)-4-(6-Amino-1-methylpyrazolo[3,4-b]pyridin-4-yl)-N-(4-methoxy-2-methylphenyl)-3-methylpiperazine-1-carboxamide To a suspension of Intermediate 6 (0.045 g, 0.18 mmol) in THF (5 mL) were added DIPEA (0.08 mmol) and 4-methoxy-2-methylphenyl isocyanate (0.028 mL). The reaction mixture was stirred at room temperature for 10 minutes. Another aliquot of 4-methoxy-2-methylphenyl isocyanate (10 μL) was added, and the reaction mixture was stirred for a further 30 minutes. The reaction mixture was concentrated to dryness, then the crude product was purified by column chromatography (silica gel 100-200 mesh, 9:1 EtOAc/MeOH), to yield the title compound (0.029 g, 38%) as a white solid. δ$_H$ (DMSO-d$_6$) 7.83 (s, 1H), 7.00 (d, J 8.0 Hz, 1H), 6.72 (d, J 2.8 Hz, 1H), 6.65 (dd, J 8.7 Hz, 1H), 5.92 (s, 1H), 5.55 (br s, 1H), 4.25-4.27 (m, 1H), 4.06-4.10 (m, 1H), 3.90-3.92 (m, 1H), 3.70 (s, 3H), 3.68 (s, 3H), 3.44-3.51 (m, 1H), 3.07-3.31 (m, 5H), 2.10 (s, 3H), 1.08 (d, J 6.4 Hz, 3H). LCMS (ES+) [M+H]$^+$ 410, RT 1.44 minutes (method 2).

Example 2

(3S)-4-(6-Amino-1-methylpyrazolo[3,4-b]pyridin-4-yl)-N-(6-methoxy-2-methylpyridin-3-yl)-3-methyl-piperazine-1-carboxamide To a solution of Intermediate 6 (0.12 g, 0.49 mmol) in acetonitrile (5 mL) was added DIPEA (170 μL, 0.98 mmol), followed by Intermediate 20 (0.11 g, 0.49 mmol). The reaction mixture was stirred at room temperature for 3 h. The reaction mixture was concentrated in vacuo, then the residue was purified by preparative HPLC, to yield the title compound (0.068 g, 34%) as a white solid. δ$_H$ (DMSO-d$_6$) 8.14 (s, 1H), 7.88 (s, 1H), 7.45 (d, J 8.6 Hz), 6.61 (d, 1H, J 8.5 Hz), 5.95 (s, 2H), 5.61 (s, 1H), 4.36-4.28 (m, 1H), 4.13 (dd, 1H, J 12.4, 0.4 Hz), 3.99 (d, 1H, J 13.2 Hz), 3.81 (s, 3H), 3.75 (s, 3H), 3.60-3.53 (m, 1H), 3.40-3.14 (m, 3H), 2.31 (s, 3H), 1.16 (d, 3H, J 6.5 Hz). LCMS (ES+) [M+H]$^+$ 411, RT 1.3 minutes (method 2).

Example 3

(3S)-4-(6-Amino-1-methylpyrazolo[3,4-b]pyridin-4-yl)-N-[6-(3,3-difluoroazetidin-1-yl)-2-methylpyridin-3-yl]-3-methylpiperazine-1-carboxamide To a solution of Intermediate 6 (0.12 g, 0.49 mmol) in acetonitrile (5 mL) was added DIPEA (170 µL, 0.98 mmol), followed by Intermediate 27 (0.155 g, 0.45 mmol). The reaction mixture was stirred at room temperature for 3 h. The reaction mixture was concentrated in vacuo, then the residue was purified by preparative HPLC, to yield the title compound (0.08 g, 30%) as a white solid. $\delta_H$ (DMSO-d$_6$) 8.00 (s, 1H), 7.79 (s, 1H), 7.29 (d, 1H, J 8.5 Hz), 6.32 (d, 1H, J 8.5 Hz), 5.87 (s, 2H), 5.53 (s, 1H), 4.49-4.22 (m, 4H), 4.09-4.01 (m, 1H), 3.90 (d, 1H, J 13.2 Hz), 3.68 (s, 3H), 3.51-3.44 (m, 1H), 3.31-3.18 (m, 3H), 3.12-3.06 (m, 1H), 2.18 (s, 3H), 1.04 (d, 3H, J 6.5 Hz). LCMS (ES+) [M+H]$^+$ 472, RT 1.5 minutes (method 2).

Example 4

(3S)—N-(6-Methoxy-2-methylpyridin-3-yl)-3-methyl-4-(1-methylpyrazolo[3,4-b]pyridin-4-yl)piperazine-1-carboxamide Intermediate 7 (0.08 g, 0.35 mmol) was dissolved in acetonitrile (7.81 g) and Intermediate 20 (0.09 g, 0.35 mmol) was added, followed by DIPEA (0.09 g, 0.69 mmol). The reaction mixture was stirred at 70° C. for 1 h, then concentrated in vacuo. The residue was purified by preparative HPLC to give the title compound (0.07 g, 51%) as a white solid. $\delta_H$ (DMSO-d$_6$) 8.24 (s, 1H), 8.19 (s, 1H), 8.11 (d, J 5.6 Hz, 1H), 7.44 (d, J 8.6 Hz, 1H), 6.61 (dd, J 8.5, 0.2 Hz, 1H), 6.43 (d, J 5.8 Hz, 1H), 4.55-4.45 (m, 1H), 4.12 (d, J 12.7 Hz, 1H), 4.04-3.85 (m, 5H), 3.81 (s, 3H), 3.52-3.37 (m, 2H), 3.30-3.20 (m, 1H), 2.28 (s, 3H), 1.20 (d, J 6.5 Hz, 3H). LCMS (ES+) [M+H]$^+$ 396, RT 1.39 minutes (method 2).

Example 5

(3S)—N-[6-(3,3-Difluoroazetidin-1-yl)-2-methylpyridin-3-yl]-3-methyl-4-(1-methylpyrazolo[3,4-b]pyridin-4-yl)piperazine-1-carboxamide Intermediate 7 (0.08 g, 0.35 mmol) was added to acetonitrile (7.81 g) and DIPEA (0.09 g, 0.69 mmol) was added, followed by Intermediate 27 (0.11 g, 0.35 mmol). The reaction mixture was stirred at 70° C. for 1 h, then concentrated in vacuo. The residue was purified by preparative HPLC to give the title compound (0.04 g, 30%) as a white solid. $\delta_H$ (DMSO-d$_6$) 8.24 (s, 1H), 8.15-8.10 (m, 2H), 7.36 (d, J 8.5 Hz, 1H), 6.44-6.37 (m, 2H), 4.57-4.42 (m, 1H), 4.33 (t, J 12.5 Hz, 4H), 4.17-3.84 (m, 6H), 3.53-3.35 (m, 2H), 3.29-3.18 (m, 1H), 2.24 (s, 3H), 1.20 (d, J 6.4 Hz, 3H). LCMS (ES+) [M+H]$^+$ 457, RT 1.56 minutes (method 2).

Example 6

(3S)—N-[6-(Difluoromethoxy)-2-methylpyridin-3-yl]-3-methyl-4-(1-methylpyrazolo[3,4-b]pyridin-4-yl)piperazine-1-carboxamide Intermediate 7 (0.06 g, 0.21 mmol) was dissolved in acetonitrile (10 mL), then DIPEA (0.05 g, 0.41 mmol) and Intermediate 22 (0.07 g, 0.23 mmol) were added. The reaction mixture was stirred at 70° C. for 1 h, then concentrated in vacuo. The residue was purified by column chromatography, using a DCM/MeOH/Et$_3$N gradient (0-10% MeOH). After freeze-drying, the title compound (0.06 g, 67.8%) was isolated as a white solid. $\delta_H$ (DMSO-d$_6$) 8.34 (m, 1H), 8.26 (m, 1H), 8.12 (d, J 5.6 Hz, 1H), 7.83-7.47 (m, 2H), 6.89 (d, J 8.5 Hz, 1H), 6.45 (m, 1H), 4.56-4.48 (m, 1H), 4.16-4.09 (m, 1H), 4.03-3.87 (m, 5H), 3.55-3.40 (m, 2H), 3.34-3.25 (m, 1H), 2.33 (s, 3H), 1.24 (m, 3H). LCMS (ES+) [M+H]$^+$ 432, RT 1.68 minutes (method 2).

Example 7

(3S)-4-(6-Amino-1-methylpyrazolo[3,4-b]pyridin-4-yl)-N-[6-(difluoromethoxy)-2-methylpyridin-3-yl]-3-methylpiperazine-1-carboxamide Intermediate 6 (0.04 g, 0.16 mmol) was dissolved in acetonitrile (10 mL) and Intermediate 22 (0.052 g, 0.18 mmol) was added, followed by DIPEA (0.069 g, 0.53 mmol). The reaction mixture was stirred at 70° C. for 1 h, then concentrated in vacuo. The residue was purified by column chromatography, using a DCM/MeOH gradient (0-5% MeOH), to yield the title compound (0.046 g, 63.3%) as a white solid. $\delta_H$ (DMSO-d$_6$) 8.31 (s, 1H), 7.91 (s, 1H), 7.83-7.46 (m, 2H), 6.89 (d, J 8.5 Hz, 1H), 5.95 (s, 2H), 5.61 (s, 1H), 4.37-4.28 (m, 1H), 4.14 (dd, J 12.6, 0.6 Hz, 1H), 4.02-3.92 (m, 1H), 3.76 (s, 3H), 3.60-3.54 (m, 1H), 3.39 (dd, J 13.3, 3.5 Hz, 1H), 3.28-3.18 (m, 2H), 2.33 (s, 3H), 1.13 (d, J 6.5 Hz, 3H). LCMS (ES+) [M+H]$^+$ 447, RT 1.58 minutes (method 2).

Example 8

(3S)-4-(6-Amino-1-methylpyrazolo[3,4-b]pyridin-4-yl)-N-(imidazo[1,2-a]pyridin-8-yl)-3-methylpiperazine-1-carboxamide Intermediate 6 (0.05 g, 0.2 mmol) was dissolved in acetonitrile (10 mL) and Intermediate 24 (0.05 g, 0.20 mmol) was added, followed by DIPEA (0.069 g, 0.53 mmol). The reaction mixture was heated at 40° C. for 2 h, then allowed to cool, and concentrated in vacuo. The residue was taken up in DCM and washed with saturated aqueous ammonium chloride solution, then dried over Na$_2$SO$_4$ and filtered. Concentration in vacuo gave an oil that was purified by column chromatography, using a DCM/MeOH gradient (0-5% MeOH), to yield the title compound (0.061 g, 74%) as a white solid. $\delta_H$ (DMSO-d$_6$) 8.33 (s, 1H), 8.20 (dd, J 6.7, 0.8 Hz, 1H), 7.97 (d, J 1.1 Hz, 1H), 7.88 (s, 1H), 7.70 (d, J 7.4 Hz, 1H), 7.55 (d, J 1.0 Hz, 1H), 6.85 (t, J 7.1 Hz, 1H), 5.96 (s, 2H), 5.59 (s, 1H), 4.42-4.34 (m, 1H), 4.14-4.07 (m, 1H), 3.97 (d, J 12.9 Hz, 1H), 3.76 (s, 3H), 3.69-3.60 (m, 1H), 3.53-3.34 (m, 3H), 1.17 (d, J 6.5 Hz, 3H). LCMS (ES+) [M+H]$^+$ 406, RT 1.33 minutes (method 2).

Example 9

(3S)-3-Ethyl-N-(6-methoxy-2-methylpyridin-3-yl)-4-(1-methylpyrazolo[3,4-b]pyridin-4-yl)piperazine-1-carboxamide Intermediate 13 (0.05 g, 0.18 mmol) was dissolved in acetonitrile (5 mL) and Intermediate 20 (0.05 g, 0.19 mmol) was added, followed by DIPEA (0.069 g, 0.53 mmol). The reaction mixture was stirred at 70° C. for 1 h, then concentrated in vacuo and partitioned between DCM and saturated aqueous ammonium chloride solution. The organic layer was loaded directly onto a silica column and purified using a DCM/MeOH gradient (0-5% MeOH). The recovered material was further purified by preparative HPLC, yielding the title compound (0.012 g, 16.0%) as a white solid. $\delta_H$ (DMSO-d$_6$) 8.24 (s, 1H), 8.19 (s, 1H), 8.11 (d, J 5.6 Hz, 1H), 7.44 (d, J 8.6 Hz, 1H), 6.61 (dd, J 8.5, 0.2 Hz, 1H), 6.43 (d, J 5.8 Hz, 1H), 4.55-4.45 (m, 1H), 4.12 (d, J 12.7 Hz, 1H), 4.04-3.85 (m, 5H), 3.81 (s, 3H), 3.52-3.37 (m, 2H), 3.30-3.20 (m, 1H), 2.28 (s, 3H), 1.72-1.63 (m, 1H), 1.55-1.44 (m, 1H), 0.91 (t, J 7.4 Hz, 3H). LCMS (ES+) [M+H]$^+$ 410, RT 1.22 minutes (method 2).

Example 10

(3S)-3-(2-Hydroxyethyl)-N-(6-methoxy-2-methyl-pyridin-3-yl)-4-(1-methylpyrazolo[3,4-b]pyridin-4-yl)piperazine-1-carboxamide Intermediate 16 was dissolved in acetonitrile (5 mL) and Intermediate 20 (0.047 g, 0.1847 mmol) was added, followed by DIPEA (0.065 g, 0.5037 mmol). The reaction mixture was stirred at 70° C. for 1 h, then concentrated in vacuo. The residue was purified by preparative HPLC to give the title compound (0.035 g, 49.61%) as a white solid. $\delta_H$ (DMSO-d$_6$) 8.32 (s, 1H), 8.17 (s, 1H), 8.10 (d, J 5.6 Hz, 1H), 7.43 (d, J 8.6 Hz, 1H), 6.60 (d, J 8.5 Hz, 1H), 6.47 (d, J 5.8 Hz, 1H), 4.79 (s, 1H), 4.42-4.41 (m, 1H), 4.20-4.05 (m, 2H), 4.00-3.90 (m, 4H), 3.81 (s, 3H), 3.59-3.44 (m, 3H), 3.40-3.20 (m, 2H), 2.27 (s, 3H), 1.92-1.70 (m, 2H). LCMS (ES+) [M+H]$^+$ 426, RT 1.10 minutes (method 2).

Example 11

(3S)—N-[4-(Difluoromethoxy)-2-methylphenyl]-3-ethyl-4-(1-methylpyrazolo[3,4-b]-pyridin-4-yl)piperazine-1-carboxamide Intermediate 13 (0.05 g, 0.18 mmol) was dissolved in acetonitrile (5 mL) and Intermediate 25 was added, followed by DIPEA (0.069 g, 0.53 mmol). The reaction mixture was stirred at 70° C. for 1 h, then concentrated in vacuo. The residue was purified by preparative HPLC to give the title compound (0.025 g, 32%) as a white solid. $\delta_H$ (DMSO-d$_6$) 8.20 (m, 2H), 8.11 (d, J 5.7 Hz, 1H), 7.35-6.93 (m, 3H), 6.97 (m, 1H), 6.43 (d, J 5.8 Hz, 1H), 4.26-4.06 (m, 3H), 3 97-3.89 (m, 4H), 3.54-3.45 (m, 1H), 3.31-3.22 (m, 2H), 2.18 (s, 3H), 1.77-1.57 (m, 2H), 0.92 (t, J 7.4 Hz, 3H). LCMS (ES+) [M+H]$^+$ 445, RT 1.88 minutes (method 2).

Example 12

(3S)—N-[4-(Difluoromethoxy)-2-methylphenyl]-3-(2-hydroxyethyl)-4-(1-methylpyrazolo-[3,4-b]pyridin-4-yl)piperazine-1-carboxamide Intermediate 16 (0.05 g, 0.17 mmol) was dissolved in acetonitrile (5 mL) and Intermediate 25 (0.047 g, 0.18 mmol) was added, followed by DIPEA (0.065 g, 0.50 mmol). The reaction mixture was stirred at 70° C. for 1 h, then concentrated in vacuo. The residue was dissolved in DCM and the organic layer was washed with aqueous ammonium chloride solution, then loaded directly onto a silica column and purified, using a DCM/MeOH gradient (0-5% MeOH), to yield the title compound (0.043 g, 55.9%) as a white solid. $\delta_H$ (DMSO-d$_6$) 8.32 (s, 1H), 8.17 (s, 1H), 8.10 (d, J 5.7 Hz, 1H), 7.40-6.90 (m, 4H), 6.47 (d, J 5.8 Hz, 1H), 4.79 (t, J 4.7 Hz, 1H), 4.49-4.41 (m, 1H), 4.20-3.95 (m, 3H), 3.95 (s, 3H), 3.57-3.22 (m, 5H), 2.16 (s, 3H), 1.92-1.70 (m, 2H). LCMS (ES+) [M+H]$^+$ 461, RT 1.62 minutes (method 2).

Example 13

(3S)-4-(6-Amino-1-methylpyrazolo[3,4-b]pyridin-4-yl)-3-ethyl-N-(6-methoxy-2-methylpyridin-3-yl)piperazine-1-carboxamide Intermediate 10 (0.05 g, 0.17 mmol) was dissolved in acetonitrile (5 mL) and Intermediate 20 (0.048 g, 0.19 mmol) was added, followed by DIPEA (0.065 g, 0.51 mmol). The reaction mixture was stirred at 70° C. for 1 h, then concentrated. The residue was purified by preparative HPLC to yield the title compound (0.031 g, 43%) as a white freeze-dried solid. $\delta_H$ (DMSO-d$_6$) 8.15 (s, 1H), 7.85 (s, 1H), 7.43 (d, J 8.5 Hz, 1H), 6.61 (d, J 8.5 Hz, 1H), 5.93 (s, 2H), 5.58 (s, 1H), 4.19-3.96 (m, 3H), 3.81 (s, 3H), 3.72 (s, 3H), 3.65-3.58 (m, 1H), 3.35-3.15 (m, 3H), 2.30 (s, 3H), 1.72-1.63 (m, 1H), 1.55-1.44 (m, 1H), 0.90 (t, J 7.4 Hz, 3H). LCMS (ES+) [M+H]$^+$ 425, RT 1.38 minutes (method 2).

Example 14

(3S)-4-(6-Amino-1-methylpyrazolo[3,4-b]pyridin-4-yl)-N-[4-(difluoromethoxy)-2-methylphenyl]-3-ethylpiperazine-1-carboxamide Intermediate 10 (0.05 g, 0.17 mmol) was dissolved in acetonitrile (5 mL) and Intermediate 25 (0.054 g, 0.19 mmol) was added, followed by DIPEA (0.065 g, 0.51 mmol). The reaction mixture was stirred at 70° C. for 1 h, then concentrated. The residue was purified by preparative HPLC to yield the title compound (0.04 g, 50%) as a white freeze-dried solid. $\delta_H$ (DMSO-d$_6$) 8.15 (s, 1H), 7.85 (s, 1H), 7.31-7.01 (m, 3H), 6.97-6.82 (m, 1H), 5.93 (s, 2H), 5.58 (s, 1H), 4.19-3.98 (m, 3H), 3.76 (s, 3H), 3.66-3.58 (m, 1H), 3.35-3.15 (m, 3H), 2.18 (s, 3H), 1.69-1.55 (m, 1H), 1.52-1.41 (m, 1H), 0.89 (t, J 7.4 Hz, 3H). LCMS (ES+) [M+H]$^+$ 460, RT 1.79 minutes (method 2).

Example 15

(3S)-4-(6-Amino-1-methylpyrazolo[3,4-b]pyridin-4-yl)-3-ethyl-N-(6-methoxy-5-methylpyridin-3-yl)piperazine-1-carboxamide Intermediate 10 (0.075 g, 0.25 mmol) was dissolved in acetonitrile (5 mL) and Intermediate 26 (0.072 g, 0.28 mmol) was added, followed by DIPEA (0.098 g, 0.76 mmol). The reaction mixture was stirred at 70° C. for 1 h, then concentrated. The residue was purified by preparative HPLC to yield the title compound (0.075 g, 70%) as a freeze-dried white solid. $\delta_H$ (DMSO-d$_6$) 8.50 (s, 1H), 8.02 (d, J 2.5 Hz, 1H), 7.85 (s, 1H), 7.64 (d, J 1.9 Hz, 1H), 5.93 (s, 2H), 5.58 (s, 1H), 4.20-4.00 (m, 3H), 3.85 (s, 3H), 3.74 (s, 3H), 3.66-3.60 (m, 1H), 3.33-3.15 (m, 3H), 2.10 (s, 3H), 1.68-1.59 (m, 1H), 1.53-1.42 (m, 1H), 0.87 (m, 3H). LCMS (ES+) [M+H]$^+$ 425, RT 1.57 minutes (method 2).

Example 16

(3S)—N-(6-Methoxy-5-methylpyridin-3-yl)-3-methyl-4-(1-methylpyrazolo[3,4-b]pyridin-4-yl)piperazine-1-carboxamide Intermediate 7 (0.1 g, 0.37 mmol) was dissolved in acetonitrile (5 mL) and Intermediate 26 (0.11 g, 0.41 mmol) was added, followed by DIPEA (0.15 g, 1.12 mmol). The reaction mixture was stirred at 70° C. for 1 h, then concentrated. The residue was purified by preparative HPLC to yield the title compound (0.08 g, 50%) as a freeze-dried white solid. $\delta_H$ (DMSO-d$_6$) 8.52 (s, 1H), 8.24 (s, 1H), 8.12 (d, J 5.6 Hz, 1H), 8.03 (d, J 2.5 Hz, 1H), 7.65 (d, J 1.9 Hz, 1H), 6.44 (d, J 5.7 Hz, 1H), 4.54-4.46 (m, 1H), 4.15-4.07 (m, 1H), 4.04-3.88 (m, 5H), 3.83 (s, 3H), 3.52-3.44 (m, 3H), 2.13 (s, 3H), 1.20 (d, J 6.5 Hz, 3H). LCMS (ES+) [M+H]$^+$ 396, RT 1.57 minutes (method 2).

Example 17

(3S)—N-(6-Ethoxy-2-methylpyridin-3-yl)-3-methyl-4-(1-methylpyrazolo[3,4-b]pyridin-4-yl)piperazine-1-carboxamide To a solution of Intermediate 7 (0.2 g, 0.86 mmol) in EtOH (5 mL) at 0° C. was added DIPEA (0.33 g, 2.58 mmol) and the reaction mixture was stirred for 10 minutes. Intermediate 23 (0.235 g, 0.86 mmol) was added. The reaction mixture was heated at 80° C. for 3 h, then concentrated in vacuo. The residue was diluted with DCM (50 mL). The organic layer was washed with water (2×30 mL) and separated, then dried over Na$_2$SO$_4$ and concentrated in vacuo. The residue was purified by silica gel (100:200 mesh) column chromatography, using 3-5% MeOH in DCM as eluent, to afford the title compound (0.13 g, 37%). $\delta_H$ (DMSO-d$_6$) 8.23 (s, 1H), 8.17-8.08 (m, 2H), 7.42 (d, J 8.5 Hz, 1H), 6.57 (d, J 8.5 Hz, 1H), 6.43 (d, J 5.7 Hz, 1H), 4.50-4.47 (m, 1H), 4.25 (q, J 7.0 Hz, 2H), 4.11 (dd, J 12.9, 4.3 Hz, 1H), 4.03-3.85 (m, 5H), 3.53-3.34 (m, 2H), 3.29-3.24 (m, 1H), 2.26 (s, 3H), 1.34-1.15 (m, 6H). LCMS (ES+) [M+H]$^+$ 410.1 (method 2).

Example 18

(3S)—N-(6-Ethoxy-2-methylpyridin-3-yl)-3-ethyl-4-(1-methylpyrazolo[3,4-b]pyridin-4-yl)-piperazine-1-carboxamide To a solution of Intermediate 13 (0.2 g, 0.81 mmol) in EtOH (5 mL) at 0° C. was added DIPEA (0.31 g, 2.43 mmol) and the reaction mixture was stirred for 10 minutes. Intermediate 23 (0.22 g, 0.81 mmol) was added. The reaction mixture was heated at 80° C. for 3 h, then concentrated in vacuo. The residue was diluted with DCM (50 mL). The organic layer was washed with water (2×30 mL) and separated, then dried over Na$_2$SO$_4$ and concentrated in vacuo. The residue was purified by silica gel (100:200 mesh) column chromatography, using 3-5% MeOH in DCM as eluent, to yield the title compound (0.13 g, 38%). $\delta_H$ (DMSO-d$_6$) 8.21 (s, 1H), 8.18-8.07 (m, 2H), 7.41 (d, J 8.5 Hz, 1H), 6.57 (d, J 8.5 Hz, 1H), 6.42 (d, J 5.8 Hz, 1H), 4.31-4.04 (m, 5H), 3.94 (s, 4H), 3.50-3.47 (m, 1H), 3.35-3.18 (m, 2H), 2.26 (s, 3H), 1.78-1.51 (m, 2H), 1.30 (t, J 7.0 Hz, 3H), 0.90 (t, J 7.4 Hz, 3H). LCMS (ES+) [M+18]$^+$441 (method 2).

Example 19

(3S)-3-Methyl-4-(1-methylpyrazolo[3,4-b]pyridin-4-yl)-N-[2-methyl-4-(trifluoro-methoxy)phenyl]piperazine-1-carboxamide To a solution of Intermediate 7 (0.15 g, 0.64 mmol) in EtOH (5 mL) at 0° C. was added DIPEA (0.248 g, 1.9 mmol) and the reaction mixture was stirred for 10 minutes. Intermediate 21 (0.192 g, 0.64 mmol) was added. The reaction mixture was heated at 80° C. for 3 h, then concentrated in vacuo. The residue was diluted with DCM (50 mL). The organic layer was washed with water (2×30 mL) and separated, then dried over Na$_2$SO$_4$ and concentrated in vacuo. The residue was purified by silica gel (100:200 mesh) column chromatography, using 3-5% MeOH in DCM as eluent, to afford the title compound (0.1 g, 34%). $\delta_H$ (DMSO-d$_6$) 8.28 (s, 1H), 8.21 (s, 1H), 8.11 (d, J 5.6 Hz, 1H), 7.31 (d, J 8.7 Hz, 1H), 7.21 (d, J 2.7 Hz, 1H), 7.13 (dd, J 8.7, 2.8 Hz, 1H), 6.43 (d, J 5.7 Hz, 1H), 4.52-4.48 (m, 1H), 4.17-4.07 (m, 1H), 4.04-3.85 (m, 5H), 3.54-3.38 (m, 2H), 3.32-3.23 (m, 1H), 2.21 (s, 3H), 1.21 (d, J 6.5 Hz, 3H). LCMS (ES+) [M+1]$^+$ 449.9 (method 2).

Example 20

(3S)-3-Ethyl-4-(1-methylpyrazolo[3,4-b]pyridin-4-yl)-N-[2-methyl-4 trifluoromethoxy)-phenyl]piperazine-1-carboxamide To a solution of Intermediate 13 (0.15 g, 0.61 mmol) in EtOH (5 mL) at 0° C. was added DIPEA (0.238 g, 1.83 mmol) and the reaction mixture was stirred for 10 minutes. Intermediate 21 (0.190 g, 0.61 mmol) was added. The reaction mixture was heated at 80° C. for 3 h, then concentrated in vacuo. The residue was diluted with DCM (50 mL). The organic layer was washed with water (2×30 mL) and separated, then dried over Na$_2$SO$_4$ and concentrated in vacuo. The residue was purified by silica gel (100:200 mesh) column chromatography, using 3-5% MeOH in DCM as eluent, to afford the title compound (0.1 g, 37%). $\delta_H$ (DMSO-d$_6$) 8.28 (s, 1H), 8.21 (s, 1H), 8.10 (d, J 5.6 Hz, 1H), 7.29 (d, J 8.7 Hz, 1H), 7.21 (d, J 2.8 Hz, 1H), 7.14 (dd, J 8.7, 2.8 Hz, 1H), 6.42 (d, J 5.7 Hz, 1H), 4.27-4.05 (m, 3H), 3.94 (s, 4H), 3.55-3.43 (m, 1H), 3.36-3.21 (m, 2H), 2.20 (s, 3H), 1.78-1.52 (m, 2H), 0.90 (t, J 7.4 Hz, 3H). LCMS (ES+) [M+1]$^+$463.1 (method 2).

Example 21

(3S)—N-(6-Isopropoxy-2-methylpyridin-3-yl)-3-methyl-4-(1-methylpyrazolo[3,4-b]-pyridin-4-yl)piperazine-1-carboxamide To a solution of Intermediate 7 (0.2 g, 0.86 mmol) in EtOH (5 mL) at 0° C. was added DIPEA (0.45 mL, 2.58 mmol) and the reaction mixture was stirred for 10 minutes. Intermediate 19 (0.25 g, 0.86 mmol) was added. The reaction mixture was heated at reflux for 3 h, then concentrated in vacuo. The residue was diluted with DCM (50 mL). The organic layer was washed with water and separated, then dried over Na$_2$SO$_4$ and concentrated in vacuo. The residue was purified by silica gel (100:200 mesh) column chromatography, using 5% MeOH in DCM as eluent, to afford the title compound (0.16 g, 43%). δ$_H$ (DMSO-d$_6$) 8.24 (s, 1H) 8.09-8.16 (m, 2H), 7.40 (d, J 8.3 Hz, 1H), 6.52 (d, J 8.8 Hz, 1H), 6.43 (d, J 5.7 Hz, 1H), 5.20 (m, 1H), 4.46-4.54 (m, 1H), 4.11 (d, J 12.7 Hz, 1H), 3.81-4.02 (m, 4H), 3.36-3.51 (m, 2H), 3.20-3.32 (m, 2H), 2.26 (s, 3H), 1.27 (d, J 6.1 Hz, 6H), 1.21 (d, J 6.6 Hz, 3H). LCMS (ES+) [M+H]$^+$ 424, RT 1.76 minutes (method 2).

Example 22

(3S)-3-Ethyl-N-(6-isopropoxy-2-methylpyridin-3-yl)-4-(1-methylpyrazolo[3,4-b]pyridin-4-yl)piperazine-1-carboxamide To a solution of Intermediate 13 (0.2 g, 0.81 mmol) in EtOH (5 mL) at 0° C. was added DIPEA (0.42 mL, 2.44 mmol) and the reaction mixture was stirred for 10 minutes. Intermediate 19 (0.23 g, 0.81 mmol) was added. The reaction mixture was heated at reflux for 3 h, then concentrated in vacuo. The residue was diluted with DCM (50 mL). The organic layer was washed with water and separated, then dried over Na$_2$SO$_4$ and concentrated in vacuo. The residue was purified by silica gel (100:200 mesh) column chromatography, using 5% MeOH in DCM as eluent, to afford the title compound (0.16 g, 45%). δ$_H$ (DMSO-d$_6$) 8.21 (s, 1H), 8.15 (s, 1H), 8.10 (d, J 6.1 Hz, 1H), 7.39 (d, J 7.9 Hz, 1H), 6.52 (d, J 8.8 Hz, 1H), 6.42 (d, J 5.2 Hz, 1H), 5.16-5.25 (m, 1H), 4.05-4.28 (m, 4H), 3.90-3.98 (m, 4H), 3.48 (t, J 10.1 Hz, 1H), 3.19-3.30 (m, 1H), 2.23 (m, 3H), 1.54-1.78 (m, 2H), 1.23-1.32 (m, 6H), 0.90 (t, J 7.5 Hz, 3H). LCMS (ES+) [M+H]$^+$ 438, RT 1.90 minutes (method 2).

Example 23

(3S)-4-(6-Amino-1-methylpyrazolo[3,4-b]pyridin-4-yl)-N-(4-methoxy-3-methylphenyl)-3-methylpiperazine-1-carboxamide Prepared from Intermediate 6 and Intermediate 32 according to the procedure described for Example 7 yielding the title compound (20 mg, 20%) as a white solid. δ$_H$ (400 MHz, DMSO-d$_6$) 8.34 (s, 1H), 7.86 (s, 1H), 7.19-7.26 (m, 2H), 6.78-6.85 (m, 1H), 5.95 (s, 2H), 5.59 (s, 1H), 4.30 (br s, 1H), 4.11 (d, J 12.49 Hz, 1H), 3.99 (d, J 13.39 Hz, 1H), 3.75 (s, 3H), 3.73 (s, 3H), 3.55 (m, 1H), 3.07-3.20 (m, 2H), 2.11 (s, 3H), 1.20-1.30 (m, 1H), 1.09 (d, J 6.25 Hz, 3H). LCMS (ES+) [M+H]$^+$ 410.0, RT 1.92 minutes (method 2).

Example 24

(3S)-4-(6-Amino-1-methylpyrazolo[3,4-b]pyridin-4-yl)-N-[5-methoxy-6-(trifluoromethyl)pyridin-2-yl]-3-methylpiperazine-1-carboxamide Prepared from Intermediate 6 and Intermediate 29 according to the procedure described for Example 7 yielding the title compound (120 mg, 42%) as a white solid. δ$_H$ (400 MHz, DMSO-d$_6$) 9.34 (s, 1H), 7.99 (d, J 9.32 Hz, 1H), 7.85 (s, 1H), 7.80 (d, J 9.32 Hz, 1H), 5.95 (s, 2H), 5.58 (s, 1H), 4.25-4.39 (m, 1H), 4.16 (d, J 12.42 Hz, 1H), 4.04 (d, J 13.31 Hz, 1H), 3.89 (s, 3H), 3.74 (s, 3H), 3.54 (d, J 12.42 Hz, 1H), 3.13-3.25 (m, 3H), 1.08 (d, J 6.65 Hz, 3H). LCMS (ES+) [M+H]$^+$ 465.0, RT 2.11 minutes (method 2).

Example 25

(3S)-4-(6-Amino-1-methylpyrazolo[3,4-b]pyridin-4-yl)-3-methyl-N-[2-methyl-4-(trifluoromethoxy)phenyl]piperazine-1-carboxamide Prepared from Intermediate 6 and Intermediate 21 according to the procedure described for Example 7 yielding the title compound (70 mg, 25%) as a white solid. δ$_H$ (400 MHz, DMSO-d$_6$) 8.20 (s, 1H), 7.84-7.92 (m, 1H), 7.30 (d, J 8.87 Hz, 1H), 7.21 (s, 1H), 7.14 (d, J 8.43 Hz, 1H), 5.95 (s, 2H), 5.59 (s, 1H), 4.27-4.38 (m, 1H), 4.13 (d, J 12.86 Hz, 1H), 3.98 (d, J 13.31 Hz, 1H), 3.75 (s, 3H), 3.56 (m, 1H), 3.37 (m, 1H), 3.15-3.30 (m, 2H), 2.21 (s, 3H), 1.12 (d, J 6.21 Hz, 3H). LCMS (ES+) [M+H]$^+$ 464.0, RT 2.29 minutes (method 2).

Example 26

(3S)-4-(6-Amino-1-methylpyrazolo[3,4-b]pyridin-4-yl)-N-[6-(dimethylamino)-2-methylpyridin-3-yl]-3-methylpiperazine-1-carboxamide Prepared from Intermediate 6 and Intermediate 33 according to the procedure described for Example 7 yielding the title compound (61 mg, 35%) as a white solid. δ$_H$ (400 MHz, DMSO-d$_6$) 7.96 (s, 1H), 7.86 (s, 1H), 7.22 (d, J 8.87 Hz, 1H), 6.43 (d, J 8.87 Hz, 1H), 5.94 (s, 2H), 5.59 (s, 1H), 4.30 (d, J 6.21 Hz, 1H), 4.12 (d, J 12.86 Hz, 1H), 3.97 (d, J 12.86 Hz, 1H), 3.75 (s, 3H), 3.54 (d, J 11.98 Hz, 1H), 3.35 (m, 1H), 3.23-3.29 (m, 1H), 3.10-3.19 (m, 1H), 2.98 (s, 6H), 2.21 (s, 3H), 1.11 (d, J 6.65 Hz, 3H). LCMS (ES+) [M+H]$^+$ 424.0, RT 1.85 minutes (method 2).

Example 27

(3S)-4-(6-Amino-1-methylpyrazolo[3,4-b]pyridin-4-yl)-3-ethyl-N-[5-methoxy-6-(trifluoromethyl)pyridin-2-yl]piperazine-1-carboxamide Prepared from Intermediate 10 and Intermediate 29 according to the procedure described for Example 13 yielding the title compound (50 mg, 27%) as a white solid. δ$_H$ (400 MHz, DMSO-d$_6$) 9.33 (s, 1H), 7.97 (d, J 9.17 Hz, 1H), 7.83 (s, 1H), 7.79 (d, J 9.17 Hz, 1H), 5.93 (s, 2H), 5.56 (s, 1H), 4.11-4.24 (m, 2H), 4.03 (br s, 1H), 3.89 (s, 3H), 3.74 (s, 3H), 3.58 (m, 1H), 3.17-3.27 (m, 3H), 1.55-1.70 (m, 1H), 1.38-1.53 (m, 1H), 0.84 (t, J 7.50 Hz, 3H). LCMS (ES+) [M+H]$^+$ 479.0, RT 2.47 minutes (method 2).

Example 28

(3S)-4-(6-Amino-1-methylpyrazolo[3,4-b]pyridin-4-yl)-3-ethyl-N-[2-methyl-4-(trifluoromethoxy)phenyl]piperazine-1-carboxamide Prepared from Intermediate 10 and Intermediate 21 according to the procedure described for Example 13 yielding the title compound (50 mg, 27%) as a white solid. δ$_H$ (400 MHz, DMSO-d$_6$) 8.22 (s, 1H), 7.84 (s, 1H), 7.29 (d, J 8.76 Hz, 1H), 7.21 (s, 1H), 7.14 (d, J 8.34 Hz, 1H), 5.93 (s, 2H), 5.57 (s, 1H), 4.06-4.22 (m, 2H), 4.00 (br s, 1H), 3.74 (s, 3H), 3.61 (m, 1H), 3.18-3.30 (m, 3H), 2.20 (s, 3H), 1.57-1.74 (m, 1H), 1.43-1.53 (m, 1H), 0.88 (t, J 7.50 Hz, 3H). LCMS (ES+) [M+H]$^+$ 478.0, RT 2.63 minutes (method 2).

Example 29

(3S)-4-(6-Amino-1-methylpyrazolo[3,4-b]pyridin-4-yl)-3-ethyl-N-(4-methoxy-2-methyl-phenyl)piperazine-1-carboxamide Prepared from Intermediate 10 and Intermediate 31 according to the procedure described for Example 13 yielding the title compound (50 mg, 31%) as a white solid. $\delta_H$ (400 MHz, DMSO-$d_6$) 8.00 (s, 1H), 7.84 (s, 1H), 7.02 (d, J 8.52 Hz, 1H), 6.77 (d, J 2.56 Hz, 1H), 6.70 (dd, J 8.52, 2.98 Hz, 1H), 5.93 (s, 2H), 5.57 (s, 1H), 4.05-4.21 (m, 2H), 3.98 (br s, 1H), 3.74 (s, 3H), 3.72 (s, 3H), 3.59 (d, J 12.36 Hz, 1H), 3.11-3.30 (m, 3H), 2.13 (s, 3H), 1.60-1.73 (m, 1H), 1.41-1.55 (m, 1H), 0.88 (t, J 7.46 Hz, 3H). LCMS (ES+) [M+H]$^+$ 424.0, RT 2.15 minutes (method 2).

Example 30

(3S)-4-(6-Amino-1-methylpyrazolo[3,4-b]pyridin-4-yl)-N-[6-(dimethylamino)-2-methylpyridin-3-yl]-3-ethylpiperazine-1-carboxamide Prepared from Intermediate 10 and Intermediate 33 according to the procedure described for Example 13 yielding the title compound (60 mg, 33%) as a white solid. $\delta_H$ (400 MHz, DMSO-$d_6$) 7.97 (s, 1H), 7.84 (s, 1H), 7.21 (d, J 8.87 Hz, 1H), 6.43 (d, J 8.87 Hz, 1H), 5.88-5.97 (m, 2H), 5.57 (s, 1H), 4.06-4.19 (m, 2H), 3.98 (br s, 1H), 3.74 (s, 3H), 3.59 (m, 1H), 3.11-3.27 (m, 3H), 2.98 (s, 6H), 2.20 (s, 3H), 1.55-1.74 (m, 1H), 1.41-1.54 (m, 1H), 0.89 (t, J 7.32 Hz, 3H). LCMS (ES+) [M+H]$^+$ 438.0, RT 1.94 minutes (method 2).

Example 31

(3S)-3-Ethyl-N-(4-isopropoxy-2-methylphenyl)-4-(1-methylpyrazolo[3,4-b]pyridin-4-yl)-piperazine-1-carboxamide Prepared from Intermediate 13 and Intermediate 30 according to the procedure described for Example 22 yielding the title compound (100 mg, 35%) as a white solid. $\delta_H$ (400 MHz, DMSO-$d_6$) 8.20 (d, J 1.1 Hz, 1H), 8.10 (dd, J 5.7, 1.1 Hz, 1H), 8.00 (s, 1H), 7.00 (d, J 8.5 Hz, 1H), 6.77-6.64 (m, 2H), 6.41 (d, J 5.7 Hz, 1H), 4.56-4.50 (m, 1H), 4.25-4.05 (m, 3H), 3.97 (s, 3H), 3.45 (d, J 11.3 Hz, 1H), 3.34-3.17 (m, 3H), 2.11 (s, 3H), 1.78-1.51 (m, 2H), 1.24 (d, J 6.1 Hz, 6H), 0.86 (t, J 7.4 Hz, 3H). LCMS (ES+) [M+H]$^+$ 437.05, RT 2.47 minutes (method 2).

Example 32

(3S)-3-Ethyl-N-[5-methoxy-6-(trifluoromethyl)pyridin-2-yl]-4-(1-methylpyrazolo[3,4-b]-pyridin-4-yl)piperazine-1-carboxamide Prepared from Intermediate 13 and Intermediate 29 according to the procedure described for Example 22 yielding the title compound (80 mg, 45%) as a white solid. $\delta_H$ (400 MHz, DMSO-$d_6$) 9.37 (s, 1H), 8.20 (s, 1H), 8.09 (d, J 5.32 Hz, 1H), 7.97 (d, J 9.31 Hz, 1H), 7.76-7.84 (m, 1H), 6.41 (d, J 5.77 Hz, 1H), 4.06-4.32 (m, 3H), 3.94 (s, 3H), 3.89 (s, 3H), 3.50 (t, J 10.42 Hz, 1H), 3.30-3.29 (m, 3H), 1.45-1.73 (m, 2H), 0.86 (t, J 7.32 Hz, 3H). LCMS (ES+) [M+H]$^+$ 464.0, RT 2.25 minutes (method 2).

Example 33

(3S)-3-Ethyl-N-(4-methoxy-3-methylphenyl)-4-(1-methylpyrazolo[3,4-b]pyridin-4-yl)-piperazine-1-carboxamide Prepared from Intermediate 13 and Intermediate 32 according to the procedure described for Example 22 yielding the title compound (200 mg, 78%) as a white solid. $\delta_H$ (400 MHz, DMSO-$d_6$) 8.36 (s, 1H), 8.21 (s, 1H), 8.10 (d, J 5.7 Hz, 1H), 7.22 (m, 2H), 6.82 (d, J 9.5 Hz, 1H), 6.42 (d, J 5.8 Hz, 1H), 4.27-4.07 (m, 3H), 3.96 (s, 3H), 3.91 (s, 1H), 3.74 (s, 3H), 3.51-3.47 (m, 1H), 3.31-3.17 (m, 2H), 2.12 (s, 3H), 1.72-1.53 (m, 2H), 0.88 (t, J 7.4 Hz, 3H). LCMS (ES+) [M+H]$^+$ 409, RT 2.02 minutes (method 2).

Example 34

(3S)-3-Ethyl-N-(4-methoxy-2-methylphenyl)-4-(1-methylpyrazolo[3,4-b]pyridin-4-yl)-piperazine-1-carboxamide Prepared from Intermediate 13 and Intermediate 31 according to the procedure described for Example 22 yielding the title compound (1.23 g, 56%) as a white solid. $\delta_H$ (400 MHz, DMSO-$d_6$) 8.21 (s, 1H), 8.10 (d, J 5.6 Hz, 1H), 8.02 (s, 1H), 7.04 (d, J 8.6 Hz, 1H), 6.78 (d, J 2.9 Hz, 1H), 6.71 (dd, J 8.6, 3.0 Hz, 1H), 6.42 (d, J 5.8 Hz, 1H), 4.25-4.06 (m, 3H), 3.96 (s, 3H), 3.90-3.88 (m, 1H), 3.73 (s, 3H), 3.51-3.43 (m, 1H), 3.33-3.21 (m, 2H), 2.12 (s, 3H), 1.77-1.56 (m, 2H), 0.91 (t, J 7.4 Hz, 3H). LCMS (ES+) [M+H]$^+$ 409, RT 1.85 minutes (method 2).

Example 35

(3S)—N-[5-(Dimethylamino)-3-methylpyrazin-2-yl]-3-ethyl-4-(1-methylpyrazolo[3,4-b]-pyridin-4-yl)piperazine-1-carboxamide Prepared from Intermediate 13 and Intermediate 34 according to the procedure described for Example 22 yielding the title compound (100 mg, 38%) as a white solid. $\delta_H$ (400 MHz, DMSO-$d_6$) 8.58 (s, 1H), 8.21 (s, 1H), 8.11 (d, J 5.6 Hz, 1H), 7.74 (s, 1H), 6.43 (d, J 5.7 Hz, 1H), 4.28-4.05 (m, 3H), 3.95 (s, 3H), 3.93-3.84 (m, 1H), 3.53-3.40 (m, 1H), 3.32 (s, 6H), 3.30-3.18 (m, 2H), 2.22 (s, 3H), 1.78-1.51 (m, 2H), 0.91 (t, J 7.4 Hz, 3H). LCMS (ES+) [M+H]$^+$ 422.0, RT 1.57 minutes (method 2).

Example 36

(3S)—N-(2,6-Dimethoxypyridin-3-yl)-3-ethyl-4-(1-methylpyrazolo[3,4-b]pyridin-4-yl)-piperazine-1-carboxamide Prepared from Intermediate 13 and Intermediate 28 according to the procedure described for Example 22 yielding the title compound (110 mg, 42%) as a white solid. $\delta_H$ (400 MHz, DMSO-$d_6$) 8.20 (s, 1H), 8.10 (d, J 5.6 Hz, 1H), 7.82 (s, 1H), 7.66 (d, J 8.3 Hz, 1H), 6.41 (d, J 5.7 Hz, 1H), 6.34 (d, J 8.3 Hz, 1H), 4.26-4.01 (m, 3H), 3.95 (s, 3H), 3.94-3.89 (m, 1H), 3.88 (s, 3H), 3.84 (s, 3H), 3.52-3.41 (m, 1H), 3.31-3.16 (m, 2H), 1.77-1.52 (m, 2H), 0.90 (t, J 7.4 Hz, 3H). LCMS (ES+) [M+H]$^+$ 426.8, RT 1.80 minutes (method 2).

Example 37

(3S)—N-(6-Bromo-5-methoxypyridin-2-yl)-3-ethyl-4-(1-methylpyrazolo[3,4-b]pyridin-4-yl)piperazine-1-carboxamide Prepared from Intermediate 13 and Intermediate 35 according to the procedure described for Example 22 yielding the title compound (120 mg, 62%) as a white solid. $\delta_H$ (400 MHz, DMSO-$d_6$) 9.38 (s, 1H), 8.19 (s, 1H), 8.09 (d, 5.7 Hz, 1H), 7.75 (d, 8.8 Hz, 1H), 7.53 (d, J 8.9 Hz, 1H), 6.41 (d, 5.8 Hz, 1H), 4.26-4.09 (m, 3H), 3.96 (s, 3H), 3.92-3.82 (m, 1H), 3.84 (s, 3H), 3.48 (t, J 12.7 Hz, 1H), 3.32-3.21 (m, 2H), 1.68-1.54 (m, 2H), 0.86 (t, J 7.4 Hz, 3H). LCMS (ES+) [M+H]$^+$ 476.0, RT 2.18 minutes (method 2).

Example 38

(3S)—N-(6-Chloro-5-methoxypyridin-2-yl)-3-ethyl-4-(1-methylpyrazolo[3,4-b]pyridin-4-yl)piperazine-1-carboxamide Prepared from Intermediate 13 and Intermediate 36 according to the procedure described for Example 22 yielding the title compound (100 mg, 36%) as a white solid. $\delta_H$ (400 MHz, DMSO-$d_6$) 9.37 (s, 1H), 8.19 (s, 1H), 8.09 (d, J 5.6 Hz, 1H), 7.75 (d, J 8.8 Hz, 1H), 7.59 (d, J 8.9 Hz, 1H), 6.40 (d, J 5.7 Hz, 1H), 4.28-4.08 (m, 3H), 3.94 (s, 3H), 3.84 (s, 3H), 3.54-3.42 (m, 1H), 3.34-3.22 (m, 3H), 1.68-1.52 (m, 2H), 0.86 (t, J 7.4 Hz, 3H). LCMS (ES+) [M+H]$^+$ 430.1, RT 2.34 minutes (method 2).

Example 39

(3S)—N-(6-Cyano-5-methoxypyridin-2-yl)-3-ethyl-4-(1-methylpyrazolo[3,4-b]pyridin-4-yl)piperazine-1-carboxamide Prepared from Intermediate 13 and Intermediate 39 according to the procedure described for Example 22 yielding the title compound (140 mg, 82%) as a white solid. $\delta_H$ (400 MHz, DMSO-$d_6$) 9.58 (s, 1H), 8.20 (s, 1H), 8.13-8.02 (m, 2H), 7.79 (d, J 9.5 Hz, 1H), 6.41 (d, J 5.8 Hz, 1H), 4.27-4.09 (m, 3H), 3.93 (s, 6H), 3.54-3.43 (m, 1H), 3.31-3.21 (m, 3H), 1.70-1.54 (m, 2H), 0.86 (t, J 7.4 Hz, 3H). LCMS (ES+) [M+H]$^+$ 421.0, RT 2.30 minutes (method 2).

The invention claimed is:

1. A compound represented by formula (IA), or a pharmaceutically acceptable salt or solvate thereof:

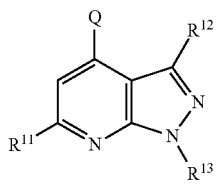

(IA)

wherein
$R^{11}$ represents hydrogen or amino;
$R^{12}$ represents hydrogen, trifluoromethyl or $C_{1-6}$ alkyl;
$R^{13}$ represents hydrogen or $C_{1-6}$ alkyl,
Q represents a group of formula (Qa),

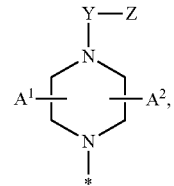

(Qa)

in which the asterisk (*) represents the point of attachment to the remainder of the molecule;
Y represents a linker group selected from —C(O)—, —C(O)N(R$^4$)— and —C(O)C(O)—;
Z represents phenyl, imidazo[1,2-a]pyridinyl, pyridinyl or pyrazinyl, any of which groups is optionally substituted by one, two or three substituents independently selected from halogen, cyano, $C_{1-6}$ alkyl, trifluoromethyl, dihalo($C_{3-7}$)-heterocycloalkyl, $C_{1-6}$ alkoxy, difluoromethoxy, trifluoro-methoxy and di($C_{1-6}$)alkylamino;
$A^1$ represents $C_{1-6}$ alkyl, optionally substituted by —OR$^a$;
$A^2$ represents hydrogen or $C_{1-6}$ alkyl;
$R^4$ represents hydrogen or $C_{1-6}$ alkyl; and
$R^a$ represents hydrogen or $C_{1-6}$ alkyl.

2. The compound as claimed in claim 1 wherein Q represents a group of formula (Qa-1), (Qa-2) or (Qa-3):

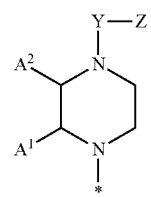

(Qa-1)

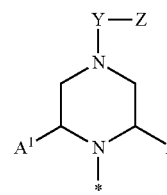

(Qa-2)

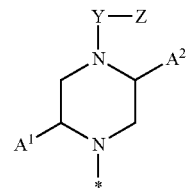

(Qa-3)

in which the asterisk (*) represents the point of attachment to the remainder of the molecule.

3. The compound as claimed in claim 1 represented by formula (IIA), or a pharmaceutically acceptable salt or solvate thereof:

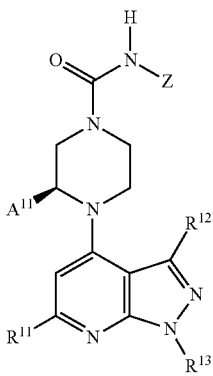

(IIA)

wherein
$A^{11}$ represents $C_{1-6}$ alkyl or —$CH_2CH_2OR^a$;
$R^{11}$ represents hydrogen or amino;
$R^{12}$ represents hydrogen, trifluoromethyl or $C_{1-6}$ alkyl; and
$R^{13}$ represents hydrogen or $C_{1-6}$ alkyl.

4. The compound as claimed in claim 1 represented by formula (IIB), or a pharmaceutically acceptable salt or solvate thereof:

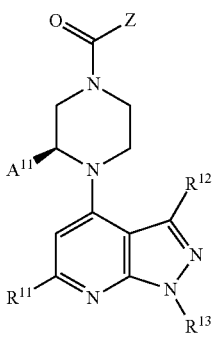

(IIB)

$R^{11}$ represents hydrogen or amino;
$R^{12}$ represents hydrogen or amino;
$R^{13}$ represents hydrogen or $C_{1-6}$ alkyl; and
$A^{11}$ represents $C_{1-6}$ alkyl or —$CH_2CH_2OR^a$.

5. The compound as claimed in claim 3 wherein $A^{11}$ represents methyl, ethyl or 2-hydroxyethyl.

6. The compound as claimed in claim 1 wherein Z represents (methoxy)(methyl)-phenyl, (isopropoxy)(methyl)phenyl, (difluoromethoxy)(methyl)phenyl, (methyl)-(trifluoromethoxy)phenyl, imidazo[1,2-a]pyridinyl, (difluoroazetidinyl)(methyl)pyridinyl, (chloro)(methoxy)pyridinyl, (bromo)(methoxy)pyridinyl, (cyano)(methoxy)pyridinyl, (methoxy)(methyl)pyridinyl, (methoxy)(trifluoromethyl)pyridinyl, dimethoxypyridinyl, (ethoxy)(methyl)pyridinyl, (isopropoxy)(methyl)pyridinyl, (difluoromethoxy)(methyl)-pyridinyl, (dimethylamino)(methyl)pyridinyl or (dimethylamino)(methyl)pyrazinyl.

7. The compound as claimed in claim 1 wherein $R^{12}$ represents hydrogen or methyl.

8. The compound as claimed in claim 1 wherein $R^{13}$ represents hydrogen or methyl.

9. The compound of formula (I), wherein the compound is (3S)-4-(6-Amino-1-methylpyrazolo[3,4-b]pyridin-4-yl)-N-(4-methoxy-2-methylphenyl)-3-methylpiperazine-1-carboxamide, (3S)-4-(6-Amino-1-methylpyrazolo[3,4-b]pyridin-4-yl)-N-(6-methoxy-2-methylpyridin-3-yl)-3-methylpiperazine-1-carboxamide, (3S)-4-(6-Amino-1-methylpyrazolo[3,4-b]pyridin-4-yl)-N-[6-(3,3-difluoroazetidin-1-yl)-2-methylpyridin-3-yl]-3-methylpiperazine-1-carboxamide, (3S)—N-(6-Methoxy-2-methylpyridin-3-yl)-3-methyl-4-(1-methylpyrazolo[3,4-b]pyridin-4-yl)piperazine-1-carboxamide, (3S)—N-[6-(3,3-Difluoroazetidin-1-yl)-2-methylpyridin-3-yl]-3-methyl-4-(1-methylpyrazolo[3,4-b]pyridin-4-yl)piperazine-1-carboxamide, (3S)—N-[6-(Difluoromethoxy)-2-methylpyridin-3-yl]-3-methyl-4-(1-methylpyrazolo[3,4-b]pyridin-4-yl)piperazine-1-carboxamide, (3S)-4-(6-Amino-1-methylpyrazolo[3,4-b]pyridin-4-yl)-N-[6-(difluoromethoxy)-2-methylpyridin-3-yl]-3-methylpiperazine-1-carboxamide, (3S)-4-(6-Amino-1-methylpyrazolo[3,4-b]pyridin-4-yl)-N-(imidazo[1,2-a]pyridin-8-yl)-3-methylpiperazine-1-carboxamide, (3S)-3-Ethyl-N-(6-methoxy-2-methylpyridin-3-yl)-4-(1-methylpyrazolo[3,4-b]pyridin-4-yl)piperazine-1-carboxamide, (3S)-3-(2-Hydroxyethyl)-N-(6-methoxy-2-methylpyridin-3-yl)-4-(1-methylpyrazolo[3,4-b]pyridin-4-yl)piperazine-1-carboxamide, (3S)—N-[4-(Difluoromethoxy)-2-methylphenyl]-3-ethyl-4-(1-methylpyrazolo[3,4-b]-pyridin-4-yl)piperazine-1-carboxamide, (3S)—N-[4-(Difluoromethoxy)-2-methylphenyl]-3-(2-hydroxyethyl)-4-(1-methylpyrazolo-[3,4-b]pyridin-4-yl)piperazine-1-carboxamide, (3S)-4-(6-Amino-1-methylpyrazolo[3,4-b]pyridin-4-yl)-3-ethyl-N-(6-methoxy-2-methyl-pyridin-3-yl)piperazine-1-carboxamide, (3S)-4-(6-Amino-1-methylpyrazolo[3,4-b]pyridin-4-yl)-N-[4-(difluoromethoxy)-2-methylphenyl]-3-ethylpiperazine-1-carboxamide, (3S)-4-(6-Amino-1-methylpyrazolo[3,4-b]pyridin-4-yl)-3-ethyl-N-(6-methoxy-5-methyl-pyridin-3-yl)piperazine-1-carboxamide, (3S)—N-(6-Methoxy-5-methylpyridin-3-yl)-3-methyl-4-(1-methylpyrazolo[3,4-b]pyridin-4-yl)piperazine-1-carboxamide, (3S)—N-(6-Ethoxy-2-methylpyridin-3-yl)-3-methyl-4-(1-methylpyrazolo[3,4-b]pyridin-4-yl)piperazine-1-carboxamide, (3S)—N-(6-Ethoxy-2-methylpyridin-3-yl)-3-ethyl-4-(1-methylpyrazolo[3,4-b]pyridin-4-yl)-piperazine-1-carboxamide, (3S)-3-Methyl-4-(1-methylpyrazolo[3,4-b]pyridin-4-yl)-N-[2-methyl-4-(trifluoro-methoxy)phenyl]piperazine-1-carboxamide, (3S)-3-Ethyl-4-(1-methylpyrazolo[3,4-b]pyridin-4-yl)-N-[2-methyl-4-(trifluoromethoxy)-phenyl]piperazine-1-carboxamide, (3S)—N-(6-Isopropoxy-2-methylpyridin-3-yl)-3-methyl-4-(1-methylpyrazolo[3,4-b]-pyridin-4-yl)piperazine-1-carboxamide, (3S)-3-Ethyl-N-(6-isopropoxy-2-methylpyridin-3-yl)-4-(1-methylpyrazolo[3,4-b]pyridin-4-yl)piperazine-1-carboxamide, (3S)-4-(6-Amino-1-methylpyrazolo[3,4-b]pyridin-4-yl)-N-(4-methoxy-3-methylphenyl)-3-methylpiperazine-1-carboxamide, (3S)-4-(6-Amino-1-methylpyrazolo[3,4-b]pyridin-4-yl)-N-[5-methoxy-6-(trifluoromethyl)pyridin-2-yl]-3-methylpiperazine-1-carboxamide, (3S)-4-(6-Amino-1-methylpyrazolo[3,4-b]pyridin-4-yl)-3-methyl-N-[2-methyl-4-(trifluoromethoxy)phenyl]piperazine-1-carboxamide, (3S)-4-(6-Amino-1-methylpyrazolo[3,4-b]pyridin-4-yl)-N-[6-(dimethylamino)-2-methyl-pyridin-3-yl]-3-methylpiperazine-1-carboxamide, (3S)-4-(6-Amino-1-methylpyrazolo[3,4-b]pyridin-4-yl)-3-ethyl-N-[5-methoxy-6-(trifluoromethyl)pyridin-2-yl]piperazine-1-carboxamide, (3S)-4-(6-Amino-1-methylpyrazolo[3,4-b]pyridin-4-yl)-3-ethyl-N-[2-methyl-4-(trifluoromethoxy)phenyl]piperazine-1-carboxamide, (3S)-4-(6-Amino-1-methylpyrazolo[3,4-b]pyridin-4-yl)-3-ethyl-N-(4-methoxy-2-methyl-phenyl)piperazine-1-carboxamide, (3S)-4-(6-Amino-1-methylpyrazolo[3,4-b]pyridin-4-yl)-N-[6-(dimethylamino)-2-methyl-pyridin-3-yl]-3-ethyl-piperazine-1-carboxamide, (3S)-3-Ethyl-N-(4-isopropoxy-2-methylphenyl)-4-(1-methylpyrazolo[3,4-b]pyridin-4-yl)-piperazine-1-carboxamide, (3S)-3-Ethyl-N-[5-methoxy-6-(trifluoromethyl)pyridin-2-yl]-4-(1-methylpyrazolo[3,4-b]-pyridin-4-yl)piperazine-1-carboxamide, (3S)-3-Ethyl-N-(4-methoxy-3-methylphenyl)-4-(1-methylpyrazolo[3,4-b]pyridin-4-yl)-piperazine-1-carboxamide, (3S)-3-Ethyl-N-(4-methoxy-2-methylphenyl)-4-(1-methylpyrazolo[3,4-b]pyridin-4-yl)-piperazine-1-carboxamide, (3S)—N-[5-(Dimethylamino)-3-methylpyrazin-2-yl]-3-ethyl-4-(1-methylpyrazolo[3,4-b]-pyridin-4-yl)piperazine-1-carboxamide, (3S)—N-(2,6-Dimethoxypyridin-3-yl)-3-ethyl-4-(1-methylpyrazolo[3,4-b]pyridin-4-yl)-piperazine-1-carboxamide, (3S)—N-(6-Bromo-5-methoxypyridin-2-yl)-3-ethyl-4-(1-methylpyrazolo[3,4-b]pyridin-4-yl)piperazine-1-carboxamide, (3S)—N-(6-Chloro-5-methoxypyridin-2-yl)-3-ethyl-4-(1-methylpyrazolo[3,4-b]pyridin-4-yl)piperazine-1-carboxamide, or (3S)—N-(6-Cyano-5-methoxypyridin-2-yl)-3-ethyl-4-(1-methylpyrazolo[3,4-b]pyridin-4-yl)piperazine-1-carboxamide.

10. A pharmaceutical composition comprising a compound of formula (I) as defined in claim 1, or a pharmaceutically acceptable salt or solvate thereof, in association with a pharmaceutically acceptable carrier.

11. A method for the manufacture of a medicament for the treatment and/or prevention of an inflammatory, autoimmune or oncological disorder; a viral disease or malaria; or organ or cell transplant rejection, the method comprising combining a compound of formula (I) as defined in claim 1, or a pharmaceutically acceptable salt or solvate thereof with a pharmaceutically acceptable carrier.

12. A method for the management of organ or cell transplant rejection, which method comprises administering to a patient in need of such treatment an effective amount of a compound of formula (I) as defined in claim 1, or a pharmaceutically acceptable salt or solvate thereof.

* * * * *